United States Patent
McMullen et al.

(10) Patent No.: US 10,534,000 B2
(45) Date of Patent: *Jan. 14, 2020

(54) METHODS FOR TREATMENT OF METASTATIC THYROID CANCER USING A PDGFR-α INHIBITOR

(71) Applicant: The Governors of the University of Alberta, Edmonton (CA)

(72) Inventors: Todd McMullen, Edmonton (CA); Raymond Lai, Saint Albert (CA)

(73) Assignee: The Governors of the University of Alberta, Edmonton (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/872,434

(22) Filed: Jan. 16, 2018

(65) Prior Publication Data
US 2018/0164318 A1 Jun. 14, 2018

Related U.S. Application Data

(63) Continuation of application No. 14/376,081, filed as application No. PCT/CA2013/000090 on Feb. 1, 2013, now Pat. No. 9,897,607.

(60) Provisional application No. 61/593,414, filed on Feb. 1, 2012.

(51) Int. Cl.
| | | |
|---|---|---|
| G01N 33/53 | (2006.01) | |
| G01N 33/574 | (2006.01) | |
| A61P 35/00 | (2006.01) | |
| C07K 16/28 | (2006.01) | |
| C07H 21/04 | (2006.01) | |
| A61K 31/4439 | (2006.01) | |
| A61K 45/06 | (2006.01) | |
| A61K 31/00 | (2006.01) | |
| A61K 31/404 | (2006.01) | |
| A61K 31/444 | (2006.01) | |
| A61K 31/713 | (2006.01) | |
| A61B 17/32 | (2006.01) | |
| A61N 5/10 | (2006.01) | |
| C12N 15/113 | (2010.01) | |

(52) U.S. Cl.
CPC ........... *G01N 33/57407* (2013.01); *A61B 17/320016* (2013.01); *A61K 31/00* (2013.01); *A61K 31/404* (2013.01); *A61K 31/444* (2013.01); *A61K 31/4439* (2013.01); *A61K 31/713* (2013.01); *A61K 45/06* (2013.01); *A61N 5/1001* (2013.01); *A61P 35/00* (2018.01); *C07H 21/04* (2013.01); *C07K 16/28* (2013.01); *C12N 15/113* (2013.01); *C12N 2310/14* (2013.01); *G01N 2333/71* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 2015/0010582 A1 | 1/2015 | Mcmullen et al. | |

FOREIGN PATENT DOCUMENTS

| | | |
|---|---|---|
| WO | WO-2007/044515 A1 | 4/2007 |
| WO | WO-2013/113102 A1 | 8/2013 |

OTHER PUBLICATIONS

"Detection of PDGFR-alpha in Formalin-Fixed, Paraffin-Embedded Rat Tissue", National Institute of Environmental Health Sciences, Immunohistochemistry Support Group (2009) retrievied from : https://www.niehs.nih.gov/research/atniehs/labs/assets/docs/k_p/pdgfralpha_508.pdf.
Brose et al., "Rationale and design of decision: a double-blind, randomized, placebo-controlled phase III trial evaluating the efficacy and safety of sorafenib in patients with locally advanced or metastatic radioactive iodine (RAI)-refractory, differentiated thyroid cancer," BMC Cancer. 11:349 (2011) (7 pages).
Bruland et al., "Inverse correlation between PDGFC expression and lymphocyte infiltration in human papillary thyroid carcinomas," BMC Cancer. 9:425 (2009) (15 pages).
Carr et al., "Phase II study of daily sunitinib in FDG-PET-positive, iodine-refractory differentiated thyroid cancer and metastatic medullary carcinoma of the thyroid with functional imaging correlation," Clin Cancer Res. 16(21):5260-8 (2010).
Chen et al., "An aberrant autocrine activation of the platelet-derived growth factor alpha-receptor in follicular and papillary thyroid carcinoma cell lines," Cancer Lett. 231(2):192-205 (2006).
Chiu et al., "Diagnostic utility of galectin-3 in thyroid cancer," Am J Pathol. 176(5):2067-81 (2010).
Cooper et al., "Revised American Thyroid Association management guidelines for patients with thyroid nodules and differentiated thyroid cancer," Thyroid. 19(11):1167-1214 (2009) (31 pages).
Cornella et al., "Molecular pathogenesis of hepatocellular carcinoma," Alcohol Clin Exp Res. 35(5):821-5 (2011).
Crowe et al., "The impact of implementation of the Bethesda System for Reporting Thyroid Cytopathology on the quality of reporting, "risk" of malignancy, surgical rate, and rate of frozen sections requested for thyroid lesions," Cancer Cytopathol. 119(5):315-21 (2011).
Dean et al., "Epidemiology of thyroid nodules," Best Pract Res Clin Endocrinol Metab. 22(6):901-11 (2008).
DeLellis, "Pathology and genetics of thyroid carcinoma," J Surg Oncol. 94(8):662-9 (2006).
Eckert et al., "Twist1-induced invadopodia formation promotes tumor metastasis," Cancer Cell. 19(3):372-86 (2011) (23 pages).

(Continued)

*Primary Examiner* — Zachary C Howard
(74) *Attorney, Agent, or Firm* — Clark & Elbing LLP

(57) ABSTRACT

Provided herein are methods for identifying a subject with an increased likelihood of developing or having metastatic papillary thyroid cancer (PTC), or a subject with an increased likelihood of developing or having recurrent PTC, and the treatment of such a subject.

11 Claims, 17 Drawing Sheets

Specification includes a Sequence Listing.

(56) References Cited

OTHER PUBLICATIONS

Elaraj et al., "Changing management in patients with papillary thyroid cancer," Curr Treat Options Oncol. 8(4):305-13 (2007).
Gharib et al., "Fine-needle aspiration biopsy of the thyroid: an appraisal," Ann Intern Med. 118(4):282-9 (1993).
Gild et al., "Multikinase inhibitors: a new option for the treatment of thyroid cancer," Nat Rev Endocrinol. 7(10):617-24 (2011).
Griffith et al., "Biomarker panel diagnosis of thyroid cancer: a critical review," Expert Rev Anticancer Ther. 8(9):1399-413 (2008).
Griffith et al., "Meta-analysis and meta-review of thyroid cancer gene expression profiling studies identifies important diagnostic biomarkers," J Clin Oncol. 24(31):5043-51 (2006).
Gu et al., "Association of XIAP and P2X7 receptor expression with lymph node metastasis in papillary thyroid carcinoma," Endocrine. 38(2):276-82 (2010).
Gupta-Abramson et al., "Phase II trial of sorafenib in advanced thyroid cancer," J Clin Oncol. 26(29):4714-9 (2008).
Homsi et al., "Spectrum of activity and mechanism of action of VEGF/PDGF inhibitors," Cancer Control. 14(3):285-94 (2007).
International Report on Patentability and the Written Opinion of the International Searching Authority for International Application No. PCT/CA2013/000090, dated Aug. 5, 2014 (8 pages).
International Search Report and Written Opinion of the International Searching Authority for International Application No. PCT/CA2013/000090, dated Apr. 29, 2013 (12 pages).
Ito et al., "Lateral lymph node dissection guided by preoperative and intraoperative findings in differentiated thyroid carcinoma," World J Surg. 32(5):729-39 (2008).
Kloos et al., "Phase II trial of sorafenib in metastatic thyroid cancer," J Clin Oncol. 27(10):1675-84 (2009).
Lee et al., "Expression of cell-cycle regulators (cyclin D1, cyclin E, p27kip1, p57kip2) in papillary thyroid carcinoma," Otolaryngol Head Neck Surg. 142(3):332-7 (2010).
Lei et al., "Pathological signaling via platelet-derived growth factor receptor alpha involves chronic activation of Akt and suppression of p53," Mol Cell Biol. 31(9):1788-99 (2011).
Liang et al., "Assessment of biomarkers for clinical diagnosis of papillary thyroid carcinoma with distant metastasis," Int J Biol Markers. 25(1):38-45 (2010).
Liu et al., "PDGF-D improves drug delivery and efficacy via vascular normalization, but promotes lymphatic metastasis by activating CXCR4 in breast cancer," Clin Cancer Res. 17(11):3638-48 (2011).
Lundgren et al., "Clinically significant prognostic factors for differentiated thyroid carcinoma: a population-based, nested case-control study," Cancer. 106(3):524-31 (2006).
Machens et al., "Pattern of nodal metastasis for primary and reoperative thyroid cancer," World J Surg. 26(1):22-8 (2002).
Marchetti et al., "A morpho-molecular diagnosis of papillary thyroid carcinoma: BRAF V600E detection as an important tool in preoperative evaluation of fine-needle aspirates," Thyroid. 19(8):837-42 (2009).
Morgenthau et al., "Recent advances in sarcoidosis," Chest. 139(1):174-82 (2011).
Nikiforov et al, "Impact of mutational testing on the diagnosis and management of patients with cytologically indeterminate thyroid nodules: a prospective analysis of 1056 FNA samples," J Clin Endocrinol Metab. 96(11):3390-7 (2011).
Nikiforov, "Thyroid carcinoma: molecular pathways and therapeutic targets," Available in PMC May 1, 2009, published in final edited form as: Mod Pathol. 21(Suppl 2):S37-43 (2008).
Provencio et al., "Clinical-molecular factors predicting response and survival for tyrosine-kinase inhibitors," Clin Transl Oncol. 11(7):428-36 (2009).
Rojo et al., "Review of imaging solutions for integrated quantitative immunohistochemistry in the Pathology daily practice," Folia Histochem Cytobiol. 47(3):349-54 (2009).
Romagnoli et al., "Targeted molecular therapies in thyroid carcinoma," Arq Bras Endocrinol Metabol. 53(9):1061-73 (2009).
Rotstein, "The role of lymphadenectomy in the management of papillary carcinoma of the thyroid," J Surg Oncol. 99(4):186-8 (2009).
Russell et al., "The alpha-receptor for platelet-derived growth factor confers bone-metastatic potential to prostate cancer cells by ligand- and dimerization-independent mechanisms," Cancer Res. 70(10):4195-203 (2010) (10 pages).
Schweppe et al., "Deoxyribonucleic acid profiling analysis of 40 human thyroid cancer cell lines reveals cross-contamination resulting in cell line redundancy and misidentification," J Clin Endocrinol Metab. 93(11):4331-41 (2008).
Shaha et al., "Patterns of failure in differentiated carcinoma of the thyroid based on risk groups," Head Neck. 20(1):26-30 (1998).
Sherman, "Targeted therapies for thyroid tumors," Mod Pathol. 24 Suppl 2:S44-52 (2011).
Shibru et al., "Does the 3-gene diagnostic assay accurately distinguish benign from malignant thyroid neoplasms?" Cancer. 113(5):930-5 (2008).
Shibru et al., "Recent developments in the clinical application of thyroid cancer biomarkers," Curr Opin Oncol. 20(1):13-8 (2008).
Sywak et al., "Routine ipsilateral level VI lymphadenectomy reduces postoperative thyroglobulin levels in papillary thyroid cancer," Surgery. 140(6):1000-7 (2006).
Taccaliti et al., "Genetic mutations in thyroid cancer," Minerva Endocrinol. 34(1):11-28 (2009).
Tambouret et al., "The clinical application and cost analysis of fine-needle aspiration biopsy in the diagnosis of mass lesions in sarcoidosis," Chest. 117(4):1004-11 (2000).
Tee et al., "Fine-needle aspiration may miss a third of all malignancy in palpable thyroid nodules: a comprehensive literature review," Ann Surg. 246(5):714-20 (2007).
Udelsman, "Treatment of persistent or recurrent papillary carcinoma of the thyroid—the good, the bad, and the unknown," J Clin Endocrinol Metab. 95(5):2061-3 (2010).
Wang et al., "Association of the T1799A BRAF mutation with tumor extrathyroidal invasion, higher peripheral platelet counts, and over-expression of platelet-derived growth factor-B in papillary thyroid cancer," Endocr Relat Cancer. 15(1):183-90 (2008).
Wang et al., "Serine phosphorylation of NPM-ALK, which is dependent on the auto-activation of the kinase activation loop, contributes to its oncogenic potential," Carcinogenesis. 32(2):146-53 (2010).
Yano et al., "Gene expression profiling identifies platelet-derived growth factor as a diagnostic molecular marker for papillary thyroid carcinoma," Clin Cancer Res. 10(6):2035-43 (2004).
Yip et al,. "Summary statement: utility of molecular marker testing in thyroid cancer," Available in PMC Dec. 1, 2011, published in final edited form as: Surgery. 148(6):1313-5 (2010) (4 pages).
Zatelli et al., "BRAF V600E mutation analysis increases diagnostic accuracy for papillary thyroid carcinoma in fine-needle aspiration biopsies," Eur J Endocrinol. 161(3):467-73 (2009).
Zhu et al., "Diagnostic significance of CK19, RET, galectin-3 and HBME-1 expression for papillary thyroid carcinoma," J Clin Pathol. 63(9):786-9 (2010) (5 pages).
International Search Report the Written Opinion of the International Searching Authority for International Application No. PCT/CA2013/000090 dated Apr. 29, 2013 (12 pages).
Nicolaou et al., "Calicheamicin theta: A Rationally Designed Molecule with Extremely Potent and Selective DNA Cleaving Properties and Apoptosis Inducing Activity," Angew Chem Int Ed Engl. 33(2): 183-6 (1994).
Castagna et al., "Limited Value of repeat recombinant human thyrotropin (rhTSH)-Stimulated Thyroglobulin Testing in Differentiated Thryoid Carcinoma Patients with Previous Negative rhTSH-Stimulated Thyroglobulin and Undetectable Basal Serum Thyroglobulin Levels," J Clin Endocrinol Metab. 93 (1): 76-81 (2008).
Coleman et al., Effectors of Humoral Immunity. Fundamental Immunology. 2nd Edition, 55-73 (1989).
Cooper et al., "Management Guidelines for Patients with Thyroid Nodules and Differentiated Thyroid Cancer", Thyroid. 16(2): 109-148 (2006).
Ho et al., "Selumetinib-Enhanced Radioiodine Uptake in Advanced Thyroid Cancer," N Engl J Med. 368(7): 623-32 (2013).

(56) References Cited

OTHER PUBLICATIONS

How et al., "Explaining the Increasing Incidence of Differentiated Thyroid Cancer," CMAJ. 177(11): 1383-84 (2007).

Loizos et al., "Targeting the Platelet-Derived Growth Factor Receptor Alpha with a Neutralizing Human Monoclonal Antibody Inhibits the Growth of Tumor Xenografts: Implications as a Potential Therapeutic Target," Mol Cancer Ther. 4(3):369-79 (2005).

Mu et al., "Combining Transfer of TTF-1 and Pax-8 gene: a Potential Strategy to Promote Radioiodine Therapy of Thyroid Carcinoma," Cancer Gene Ther. 19 (6): 402-11 (2012).

Rotstein, "The Role of Lymphadenectomy in the Management of Papillary Carcinoma of the Thyroid", J Surg Oncol. 99(4): 186-88 (2009).

Sakorafas et al., "Cervical lymph Node Dissection in Papillary Thyroid Cancer: Current Trends, Persisting Controversies, and Unclarified Uncertainties," Surg Oncol. 19(2): e57-e70 (2010).

Verbeek et al., "The Effects of Four Different Tyrosine Kinase Inhibitors on Medullary and Papillary Thyroid Cancer Cells," J Clin Endocrinol Metab. 96(6): E991-E995 (2011).

Zhang et al., "Platelet-Derived Growth Factor Receptor-Alpha Promotes Lymphatic Metastases in Papillary Thyroid Cancer," J Pathol. 228 (2): 241-50 (2012).

International Search Report for International Application No. PCT/IB2015/001426, dated Nov. 19, 2015 (5 pages).

International Preliminary Report on Patentability for International Application No. PCT/IB2015/001426, dated Nov. 19, 2015 (9 pages).

Aparicio-Gallego et al., "New insights into molecular mechanisms of sunitinib-associated side effects," Mol Cancer Ther. 10(12):2215-23 (2011).

NIH Clinical Trial NCT01321554: A Multicenter, Randomized, Double-Blind, Placebo-Controlled, Phase 3 Trial of Lenvatinib (E7080) in 131I-Refractory Differentiated Thyroid Cancer (DTC) (Select), published Mar. 23, 2011 (8 pages).

Tohyama et al., "Antitumor activity of lenvatinib (e7080): an angiogenesis inhibitor that targets multiple receptor tyrosine kinases in preclinical human thyroid cancer models," J Thyroid Res. 2014:638747, 2014 (14 pages).

NIH Clinical Trial NCT01229644: A Phase II Study of Crenolanib (CP-868,596), a Selective and Potent Inhibitor of PDGFR, for the Treatment of Adult Gliomas, published Oct. 28, 2010 (6 pages).

Office Action for Canadian Patent Application No. 2,863,427, dated Feb. 26, 2019 (4 pages).

Final Office Action for U.S. Appl. No. 15/304,394, dated Sep. 18, 2018 (20 pages).

Notice of Allowance for U.S. Appl. No. 15/304,394, dated Dec. 19, 2018 (7 pages).

Notice of Allowance for U.S. Appl. No. 14/376,081, dated Oct. 16, 2017 (5 pages).

Final Office Action for U.S. Appl. No. 14/376,081, dated Apr. 14, 2017 (19 pages).

Non-Final Office Action for U.S. Appl. No. 15/304,394, dated Jan. 16, 2018 (12 pages).

Restriction Requirement for U.S. Appl. No. 15/304,394, dated Aug. 21, 2017 (7 pages).

B
Primary tumour with lymph node metastases

C
Lymph node with tumour metastases

A

Error bars indicate P<0.01

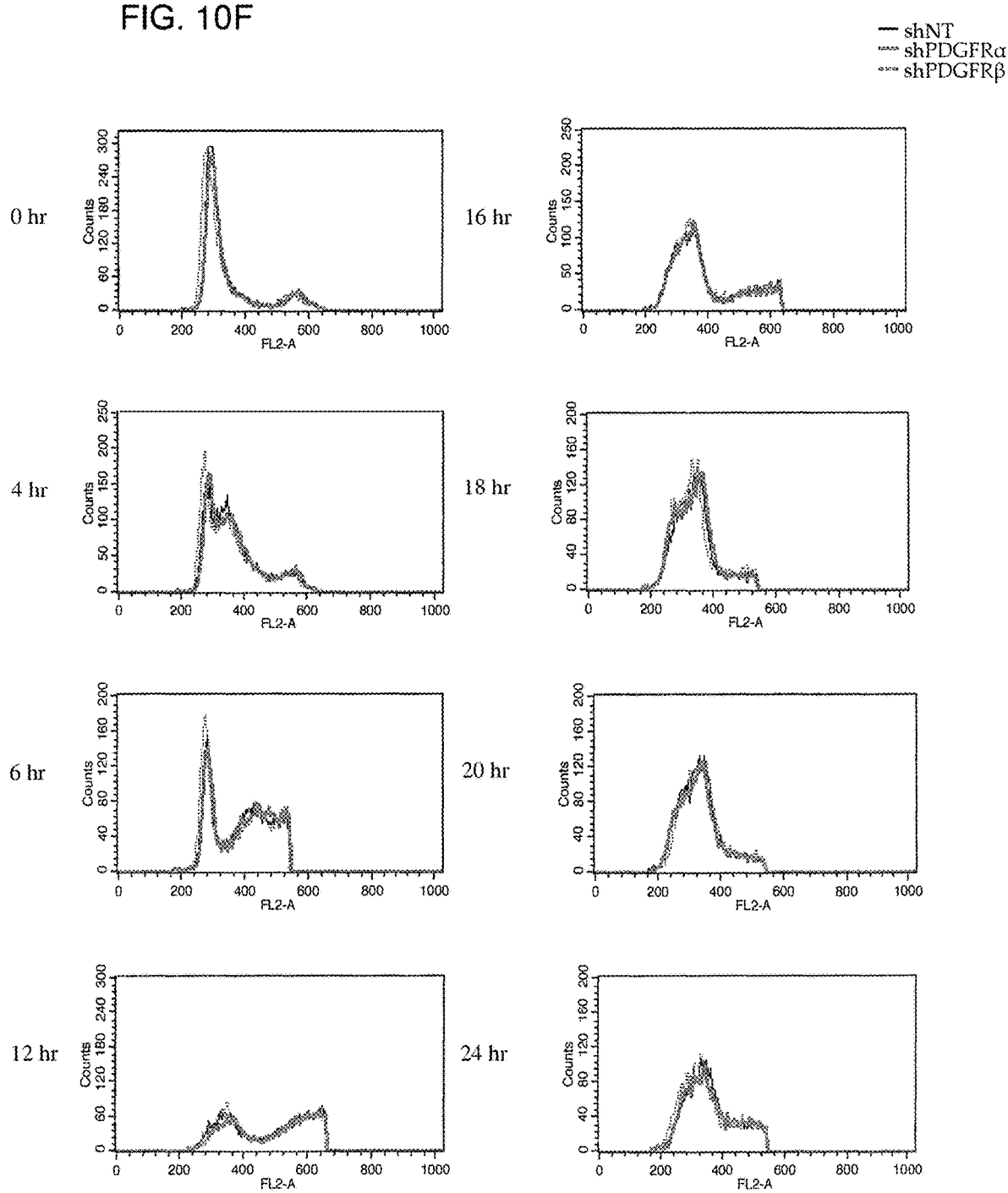

BCPAP-Tight-Pur(empty vector)

f

BCPAP-Tight-Pur-PDGFRα

FIG. 15

| Symbol | Well | AVG ΔCt (Ct(GOI) – AVE Ct (HKG)) | | 2^ΔCt | | Fold Difference | T-Test | Fold Up- or Down-Regulation |
|---|---|---|---|---|---|---|---|---|
| | | Mets | 1 tumor | Mets | 1 tumor | Mets1/tumor | pvalue | Mets1/tumor |
| HSPB1 | C09 | 0.90 | 1.07 | 5.3E-01 | 4.8E-01 | 1.12 | 0.683558 | 1.12 |
| IGF1 | C10 | 6.92 | 7.86 | 8.3E-03 | 4.3E-03 | 1.92 | 0.941909 | 1.92 |
| IGF1R | C11 | 2.74 | 2.50 | 1.5E-01 | 1.8E-01 | 0.85 | 0.301352 | -1.18 |
| ILK | C12 | 4.78 | 5.29 | 3.6E-02 | 2.6E-02 | 1.42 | 0.818269 | 1.42 |
| IRAK1 | D01 | 7.33 | 7.68 | 6.2E-03 | 4.9E-03 | 1.27 | 0.326672 | 1.27 |
| IRS1 | D02 | 7.18 | 8.30 | 6.9E-03 | 3.2E-03 | 2.18 | 0.053860 | 2.18 |
| ITGB1 | D03 | 0.87 | 0.90 | 5.5E-01 | 5.4E-01 | 1.02 | 0.903565 | 1.02 |
| JUN | D04 | 3.14 | 5.60 | 1.1E-01 | 2.1E-02 | 5.52 | 0.000670 | 5.52 |
| MAP2K1 | D05 | 6.24 | 6.36 | 1.3E-02 | 1.2E-02 | 1.09 | 0.938994 | 1.09 |
| MAPK1 | D06 | 2.08 | 1.98 | 2.4E-01 | 2.5E-01 | 0.93 | 0.583627 | -1.07 |
| MAPK14 | D07 | 3.80 | 3.85 | 7.2E-02 | 6.9E-02 | 1.04 | 0.859373 | 1.04 |
| MAPK3 | D08 | 7.12 | 7.06 | 7.2E-03 | 7.5E-03 | 0.96 | 0.531688 | -1.04 |
| MAPK8 | D09 | 3.38 | 3.43 | 9.6E-02 | 9.3E-02 | 1.04 | 0.966959 | 1.04 |
| MTCP1 | D10 | 5.01 | 5.01 | 3.1E-02 | 3.1E-02 | 1.00 | 0.856205 | 1.00 |
| MYC | D11 | 4.93 | 5.15 | 3.3E-02 | 2.8E-02 | 1.16 | 0.848495 | 1.16 |
| NFKB1 | D12 | 2.98 | 2.77 | 1.3E-01 | 1.5E-01 | 0.86 | 0.492517 | -1.16 |
| NFRSIA | E01 | 1.64 | 1.87 | 3.2E-01 | 2.7E-01 | 1.18 | 0.930276 | 1.18 |
| PABPC1 | E02 | 0.35 | 0.40 | 7.8E-01 | 7.5E-01 | 1.04 | 0.960104 | 1.04 |
| PAK1 | E03 | 4.21 | 4.71 | 5.4E-02 | 3.8E-02 | 1.42 | 0.117743 | 1.42 |
| PDGFRA | E04 | 4.60 | 7.14 | 3.6E-02 | 7.1E-03 | 5.08 | 0.013714 | 5.08 |
| PDK1 | E05 | 5.19 | 5.36 | 2.7E-02 | 2.4E-02 | 1.14 | 0.992160 | 1.14 |
| PDK2 | E06 | 6.79 | 7.27 | 9.0E-03 | 6.5E-03 | 1.39 | 0.172118 | 1.39 |
| PDPK1 | E07 | 4.96 | 5.05 | 3.2E-02 | 3.0E-02 | 1.07 | 0.683228 | 1.07 |
| PIK3CA | E08 | 3.79 | 3.73 | 7.2E-02 | 7.5E-02 | 0.96 | 0.726016 | -1.04 |
| PIK3CG | E09 | 6.87 | 7.17 | 8.5E-03 | 6.9E-03 | 1.23 | 0.757730 | 1.23 |
| PIK3R1 | E10 | 3.37 | 3.27 | 9.7E-02 | 1.0E-01 | 0.94 | 0.637406 | -1.07 |
| PIK3R2 | E11 | 8.71 | 8.47 | 2.4E-03 | 2.8E-03 | 0.86 | 0.417633 | -1.16 |
| PRKCA | E12 | 6.94 | 7.44 | 8.0E-03 | 5.7E-03 | 1.40 | 0.885143 | 1.40 |
| PRKCB | F01 | 6.56 | 5.80 | 1.1E-02 | 1.8E-02 | 0.59 | 0.251323 | -1.70 |
| PRKCZ | F02 | 4.48 | 4.45 | 4.5E-02 | 4.5E-02 | 1.01 | 0.938207 | 1.01 |
| PTEN | F03 | 1.34 | 1.38 | 3.9E-01 | 3.8E-01 | 0.93 | 0.962927 | 1.03 |
| PTK2 | F04 | 3.47 | 3.92 | 9.0E-02 | 6.6E-02 | 1.37 | 0.031728 | 1.37 |
| PTPN11 | F05 | 3.16 | 3.00 | 1.1E-01 | 1.3E-01 | 0.90 | 0.518097 | -1.11 |
| RAC1 | F06 | 0.61 | 1.05 | 6.5E-01 | 4.8E-01 | 1.36 | 0.006677 | 1.36 |
| RAF1 | F07 | 3.24 | 3.28 | 1.1E-01 | 1.0E-01 | 1.03 | 0.970010 | 1.03 |
| RASA1 | F08 | 1.89 | 1.88 | 2.7E-01 | 2.7E-01 | 0.99 | 0.764223 | -1.01 |
| REC2 | F09 | 3.92 | 3.86 | 6.6E-02 | 6.9E-02 | 0.96 | 0.748847 | -1.04 | ns

SEQUENCE LISTING

```
<160> NUMBER OF SEQ ID NOS: 4

<210> SEQ ID NO 1
<211> LENGTH: 29
<212> TYPE: DNA
<213> ORGANISM: Homo sapiens

<400> SEQUENCE: 1
gatgcctggc taagaatctc cttggagct                                       29

<210> SEQ ID NO 2
<211> LENGTH: 29
<212> TYPE: DNA
<213> ORGANISM: Homo sapiens

<400> SEQUENCE: 2
agttccacct tcatcaagag agaggacga                                       29

<210> SEQ ID NO 3
<211> LENGTH: 29
<212> TYPE: DNA
<213> ORGANISM: Homo sapiens

<400> SEQUENCE: 3
tgcctccgac gagatctatg agatcatgc                                       29

<210> SEQ ID NO 4
<211> LENGTH: 29
<212> TYPE: DNA
<213> ORGANISM: Homo sapiens

<400> SEQUENCE: 4
accttctcca gcgtgctcac actgaccaa                                       29
```

METHODS FOR TREATMENT OF METASTATIC THYROID CANCER USING A PDGFR-α INHIBITOR

RELATED APPLICATIONS

This application claims priority to U.S. Application No. 61/593,414 filed Feb. 1, 2012, the contents all of which are hereby incorporated by reference in their entirety.

FIELD OF THE INVENTION

The field of the invention generally relates to compositions and methods for identifying a subject with an increased likelihood of developing or having metastatic papillary thyroid cancer (PTC), as well as the treatment of such a subject population.

BACKGROUND OF THE INVENTION

Clinical or radiographic identification of thyroid nodules requires assessment for malignancy through tissue biopsy.[1,2] Typically obtained through fine needle aspiration (FNA), thyroid nodule biopsy can distinguish cancer from benign disease in approximately 65% of cases in large series and is considered essential in the workup of any thyroid nodule.[1,3] Improvements in the accuracy of tissue biopsy have utilized ultrasound and a standardized pathology reporting system.[4]

Efforts to extend the utility of this tissue resource are now focused primarily on molecular methods to better predict the natural history of disease and tailor patient therapy.[5] Papillary thyroid cancer (PTC), comprising more than 80% of all thyroid cancer cases, has a high propensity for spread within the lymphatic system.[6] However, one important limitation of current FNA assessment is that no information is provided on the metastatic potential of thyroid malignancy.[3,5,7] Up to 30% of papillary thyroid carcinoma cases demonstrate lymphatic metastases which, if untreated through surgery or radioactive iodine ablation, may lead to recurrent disease in the central or lateral neck.[6,8-10] Patients with metastatic or recurrent PTC often require multiple surgical resections and radioactive iodine ablative treatments with associated increased morbidity.[9-12] Predicting aggressive or metastatic variants through tissue biopsy could direct surgeons to prophylactic neck dissections and guide adjuvant radioiodine therapy to decrease the risk of local and regional recurrence and improve quality-of-life.[11-13]

In the drive to develop molecular techniques to make more personalized choices for patient diagnosis and therapy, a large number of studies on the mitogen-activated protein kinase (MAPK/ERK) signaling pathway have been undertaken to understand the pathogenesis of thyroid cancer.[14,15] It is understood that rearrangements of tyrosine kinase genes RET/PTC and activating mutations of the BRAF or RAS commonly activate the MAPK/ERK pathway.[16-18] BRAF, an isoform of a class of serine-threonine kinases, is also a potent activator of this pathway and the V600E mutation is an important and well conserved mutation in papillary thyroid cancer.[17] Activating mutations of the RAS genes, namely H-/K-/N-ras, also play an important role in the pathogenesis of papillary thyroid cancer through the MAPK/ERK pathway.[18,19] Other genotype-phenotype correlations have been undertaken in thyroid cancer using gene arrays to develop predictive tools based on galectin-3, cell cycle proteins and apoptotic markers.[19-25] RET/PTC translocations and activating mutations of BRAF and RAS genes are considered clinically relevant markers that have been endorsed for use by the American Thyroid Association in the diagnosis of thyroid cancer when tumor cytology is indeterminate.[5,25] At this time these genetic testing regimes are utilized selectively in only a few high-volume centers. While studies of diagnostic biomarkers for thyroid cancer dominate the literature, relatively few studies have examined the pathways and processes mediating lymphatic or distant spread in thyroid cancer. Research into biomarkers for lymphatic metastases reveal a number of changes in cell cycle proteins (cyclin D1), angiogenesis (vascular endothelial growth factor-VEGF), and metalloproteinases (MMP-2) but none are clinically accepted for use.[26-29]

Platelet derived growth factors (PDGFs) are a family of peptides that bind to tyrosine kinase receptors (PDGF subunits α and β) and stimulate cell survival, growth, and proliferation.[30] PDGF promotes the epithelial to mesenchymal transition (EMT), an important process in tumor metastases, and complements the function of VEGF in angiogenesis.[30,31]

It is, therefore, desirable to provide compositions and/or methods for identifying a subject with an increased likelihood of developing or having metastatic papillary thyroid cancer (PTC).

This background information is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

In accordance with one aspect of the present invention there is provided herein a method for identifying a subject with an increased likelihood of developing or having metastatic papillary thyroid cancer (PTC), or a subject with an increased likelihood of developing or having recurrent PTC.

In accordance with one aspect of the present invention, there is provided a method for treating a subject with or suspected of having papillary thyroid cancer, comprising: a) obtaining a tumor sample from a subject having thyroid cancer; b) processing said sample; c) performing an analyte binding assay configured to detect a biomarker in said processed tumor sample by introducing the processed tumor sample into an assay instrument which (i) contacts a reagent which specifically binds for detection of the biomarker within the tumor sample, and (ii) generates one or more assay results indicative of binding of said biomarker, d) administering a treatment for papillary thyroid cancer to said subject when the amount of the biomarker in the sample is greater than that in a control sample, wherein said biomarker is platelet-derived growth factor receptor α (PDGFR-α).

In accordance with one aspect of the present invention, there is provided a method comprising: a) obtaining a sample from a subject with thyroid cancer; b) processing said sample; c) performing an analyte binding assay comprising contacting the processed sample with a reagent to form a complex between the reagent and the biomarker present in the sample; d) generating a result using instrumentation configured to detect said complex, said result indicative of the amount or concentration of said complex formed to determine the amount or concentration of said biomarker in the sample; and e) administering a treatment for papillary thyroid cancer to said subject when the amount of the biomarker in the sample is greater than that in a control sample, wherein said biomarker is PDGFR-α.

In accordance with one aspect of the present invention, there is provided a method comprising: a) performing an analyte binding assay comprising contacting a processed sample, said processed sample obtained from a subject with thyroid cancer, with a reagent to form a complex between the reagent and the biomarker present in the sample; b) generating a result indicative of the amount or concentration of said complex formed to determine the amount or concentration of said biomarker in the sample; and c) administering a treatment for papillary thyroid cancer to said subject when the amount of the biomarker in the sample is greater than that in a control sample, wherein said biomarker is PDGFR-α.

In some examples, said biomarker is a biomarker protein, a biomarker transcript, or biomarker activity.

In some examples, said analyte binding assay in an immunoassay.

In some examples, wherein said immunoassay is immunohistochemistry.

In some examples, said analyte binding assay is an RNA detecting assay.

In some examples, said RNA detecting assay comprises RT-PCR or in situ hybridization.

In some examples, wherein said immunohistochemistry is performed with an automated system, or a manual system.

In some examples, said assay results quantitative or semi-quantitative.

In some examples, wherein said processing comprises formalin fixing, paraffin-embedding, snap freezing, treated to isolate DNA, RNA, or protein, or any combination thereof, said sample.

In some examples, said treatment comprises surgical resection, radio therapy, chemotherapy, or combinations thereof.

In some examples, said radio therapy comprises radio iodine ablative therapy.

In some examples, said chemotherapy comprises a tyrosine kinase inhibitor such as sorafenib, sunitinib, axitinib, or motisanib.

In some examples, said chemotherapy comprises a tyrosine kinase inhibitor such as sorafenib, sunitinib, axitinib, or motesanib.

In some examples, said inhibitor comprises, an RNA interference molecule, a small molecule, nucleic acid, an antibody, a peptide, a pharmaceutical composition, an aptamers, or combinations thereof.

In some examples, said RNA interference molecule comprises a RNAi molecule, a siRNA molecule, or a shRNA molecule.

In accordance with one aspect of the present invention, there is provided a system for treating a subject with or suspected of having papillary thyroid cancer, comprising: a) a reagent which specifically binds for detection of PDGFR-α in a tumor sample from a patient with thyroid cancer, and b) an assay instrument configured to receive a tumor sample and contact the reagent with the tumor sample, and to generate one or more assay result indicative of binding said reagent with the PDGRF-α within the tumor sample which is assayed for specific binding.

In some examples, said assay instrument comprises a detector set to detect a complex between said reagent and the PDGFR-α within the tumour sample, and wherein the instrument generates an assay results.

In some examples, the reagent is specific for PDGFR-α protein, PDGFR-α transcript, or PDGFR-α activity.

In some examples, the system further comprising a treatment for papillary thyroid cancer for said subject when the amount of the PDGFR-α in the sample is greater than that in a control sample.

In some examples, said treatment comprises surgical resection, radio therapy, chemotherapy, or combinations thereof.

In some examples, said radio therapy comprises radio iodine ablative therapy.

In some examples, said chemotherapy comprises, sorafenib, sunitinib, axitinib, or motisanib.

In some examples, said chemotherapy comprises, sorafenib, sunitinib, axitinib, or motesanib.

In some examples, said inhibitor comprises, an RNA interference molecule, a small molecule, nucleic acid, an antibody, a peptide, a pharmaceutical composition, an aptamers, or combinations thereof.

In some examples, said RNA interference molecule comprises a RNAi molecule, a siRNA molecule, or a shRNA molecule.

In accordance with one aspect of the present invention, there is provided a kit for treating a subject with or suspected of having papillary thyroid cancer, comprising: a) a reagent for performing an analyte binding assay comprising contacting a processed sample from a subject with thyroid cancer with said reagent to form a complex between the reagent and a biomarker present in the sample, wherein said biomarker is PDGFRα; and b) instructions for treating a subject with or suspected of having papillary thyroid cancer according to the methods as described herein.

In some examples, said reagent comprises an agent which binds to PDGFRα transcript or PDGFRα protein.

In some examples, said reagent comprises an antibody.

In accordance with one aspect of the present invention, there is provided use of an inhibitor of PDGFRα for the treatment of a subject with or suspected of having metastatic or recurrent PTC.

In some examples, wherein said subject is determined as having or suspected as having metastatic or recurrent PTC by performing a) an analyte binding assay comprising contacting a processed sample from said subject with a reagent to form a complex between the reagent and a biomarker present in the sample; and b) generating a result using instrumentation configured to detect said complex, said result indicative of the amount or concentration of said complex formed to determine the amount or concentration of said biomarker in the sample; wherein said subject is determined as having or suspect as having PCT when the amount of the biomarker in said processed sample is greater than a control.

In some examples, said biomarker is a biomarker protein, a biomarker transcript, or biomarker activity.

In some examples, said analyte binding assay in an immunoassays.

In some examples, said immunoassay is immunohistochemistry.

In some examples, said analyte binding assay is an RNA detecting assay.

In some examples, said RNA detecting assay comprises RT-PCR or in situ hybridization.

In some examples, said immunohistochemistry is performed with an automated system, or a manual system.

In some examples, said assay results quantitative or semi-quantitative.

In some examples, said processing comprises formalin fixing, or paraffin-embedding, or both formalin fixing and paraffin-embedding, said sample.

In some examples, said inhibitor comprises, an RNA interference molecule, a small molecule, nucleic acid, an antibody, a peptide, a pharmaceutical composition, an aptamers, or combinations thereof.

In some examples, said RNA interference molecule comprises a RNAi molecule, a siRNA molecule, or a shRNA molecule.

In some examples, said use further comprising the use of radio therapy, chemotherapy, or combinations thereof.

In some examples, said radio therapy comprises radio iodine ablative therapy.

In some examples, wherein said chemotherapy comprises a tyrosine kinase inhibitor.

In some examples, wherein said chemotherapy comprises sunitinib, axitinib, or motisanib.

BRIEF DESCRIPTION OF THE DRAWINGS

In some examples, wherein said chemotherapy comprises sunitinib, axitinib, or motesanib.

FIG. 15 shows that PDGFR-alpha mRNA levels are greater in metastatic specimens than in primary tumours.

Figure 1:
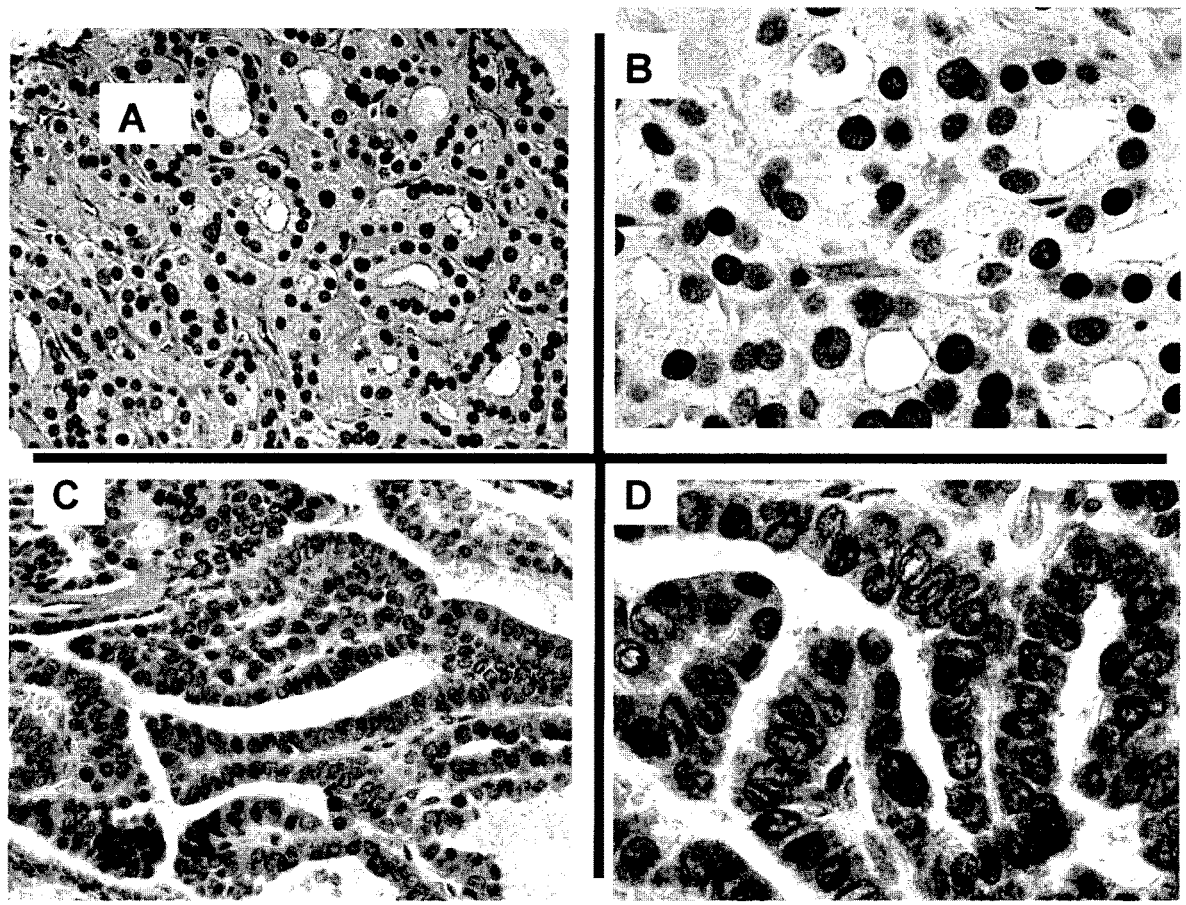
FIG. 1 shows representative immunohistochemical stains of PDGFR-α in papillary thyroid cancer (PTC) primary tumors without nodal metastases at low power (A) (100×) and high power (B) (400×), primary tumors with nodal metastases are shown (C) (100×) and (D) (400×)

In the Detailed Description that follows, the numbers in bold face type serve to identify the component parts that are described and referred to in relation to the drawings depicting various embodiments of the invention. It should be noted that in describing various embodiments of the present invention, the same reference numerals have been used to identify the same of similar elements. Moreover, for the sake of simplicity, parts have been omitted from some figures of the drawings.

DETAILED DESCRIPTION

As will be described in more detail below, in one embodiment, there is provided herein a method for identifying a subject with an increased likelihood of developing or having metastatic cancer, or a subject with an increased likelihood of developing or having recurrent cancer. There is also provided the treatment of such a subject population.

In one embodiment, there is provided herein a method for identifying a subject with an increased likelihood of developing or having metastatic papillary thyroid cancer (PTC), or a subject with an increased likelihood of developing or having recurrent PTC. There is also provided methods of treatment of this subject population.

In some examples, the subject is at risk for PTC, or is suspected of having PTC, and/or has been diagnosed with PTC.

The term "subject at risk for PTC" as used herein, refers to a subject with one or more risk factors for developing PTC. Risk factors include, but are not limited to, gender, age, genetic predisposition, previous incidents with cancer, and pre-existing non-cancer diseases.

The term "subject suspected of having PTC" as used herein, refers to a subject that presents one or more symptoms indicative of PTC or that is being screened for PTC (e.g., during an examination). A subject suspected of having PTC may also have one or more risk factors. The term encompasses individuals who have not been tested for PTC, individuals who have received an initial diagnosis (e.g., a CT scan showing a mass) but for whom the stage of cancer is not known, as well as individuals for whom the stage and/or grade of cancer has been determined by a conventional method (e.g., Gleason score). The term also includes patients who have previously undergone therapy for PTC.

The term "subject diagnosed with PTC" as used herein, refers to a subject who has been tested and found to have PTC. The diagnosis may be performed using any suitable method, including, but not limited to, biopsy, x-ray, blood test, and the methods of the present invention.

The term "subject" or "patient" as used herein, refers to any mammal or non-mammal that would benefit from determining the benefit from treatment, treatment, diagnosis, therapeutic monitoring, and/or prognosis. In certain examples a subject or patient includes, but is not limited to, humans, farm animals (cows, sheep, pigs, and the like), companion animals (such as cats, dogs and horses, and the like), non-human primates and rodent (such as mice and rats). In a specific embodiment, the subject is a human.

The identification of a subject having increased likelihood of developing PTC or having metastatic PCT or recurrent (PTC), indicates that such a subject is a candidate for treatment of such metastatic or recurrent PTC.

The term "treatment" as used herein, refers to clinical intervention in an attempt to alter the course of the subject or cell being treated. In non-limiting examples, treatment includes preventing or delaying recurrence of disease, alleviation of symptoms, diminishment of any direct or indirect pathological consequences of the disease, preventing metastasis, decreasing the rate of disease progression, amelioration or palliation of the disease state, and remission or improved prognosis. In some examples such treatment decreases the risk of local and regional recurrence and improves quality-of-life of said subject.

Treatment of papillary thyroid carcinoma includes, at a minimum, total thyroidectomy with a possible lymph node dissection in the central compartment of the neck to remove local metastatic deposits. The decision to proceed with lymph node dissection is at the discretion of the surgeon and depends on the preoperative investigation including ultrasound and clinical examination. Following surgery radioactive iodine is given to patients especially those patients with tumors larger than 1.5 cm per those patients with concerning features on pathology including signs of vascular and lymphatic invasion in the tumor specimen. External beam radiation therapy may be used in a small percentage of cases if the papillary thyroid carcinoma is extremely aggressive and it is invading outside of the thyroid and involving the muscles in the neck or the trachea or esophagus. In cases of recurrent papillary thyroid carcinoma all of the previous treatment modalities including surgery, radioactive iodine, external beam radiotherapy may be used depending on the size and site of recurrence and if it is amenable to surgical resection. In cases that fail these methods of treatment clinical trials (for example Phase I clinical trials) are used to test the possibility that tyrosine kinase inhibitors may slow the growth of the tumor.

In one example, treatment of metastatic PTC or recurrent PTC includes, but is not limited to, neck dissections (including prophylactic neck dissections) and/or adjuvant radioiodine therapy.

In one example, treatment of metastatic PTC or recurrent PTC includes, but is not limited to, administration of a pharmaceutical composition. In some examples, the pharmaceutical composition is a tyrosine kinase inhibitor. In some examples, the pharmaceutical composition comprises sorafenib, sunitinib, axitinib, or motesanib.

Thus, in some examples, the methods as described herein are useful in determining the benefit from treatment of a subject with cancer.

The term "cancer" as used herein, refers to or describes the physiological condition in a subject, such as a mammal, that is typically characterized by unregulated cell growth In some examples, the methods as described herein are useful in determining the benefit of treatment of a subject with a cancer that is spread via the lymphatic system. Examples include, breast cancer, colon cancer, and PTC. In a specific example said cancer is PTC.

The term "determining the benefit from treatment" as used herein, generally refers to assessing whether a patient is a suitable candidate for treatment. The patient may be at risk of having cancer (such as PTC), or suspected of having cancer (such as PTC), or has been diagnosed with cancer (such as PTC), or has an increased likelihood of developing metastatic cancer (such as PTC). In some examples, a patient which is determined to benefit from treatment is a suitable candidate for surgery, and/or radiation therapy (such as radioactive iodine ablation), and/or chemotherapy.

There is provided herein a method for identifying a subject with increased likelihood of developing or having metastatic or recurrent cancer, comprising determining the presence of a prognostic marker in a sample of said patient.

In another example, there is provided herein a method for identifying a subject with increased likelihood of developing or having metastatic or recurrent papillary thyroid cancer (PTC), comprising determining the presence of a prognostic marker in a sample of said patient.

In one example, a method as described herein comprises qualitatively or quantitatively determining, analyzing or measuring a biological sample from a subject for the presence or absence, or amount or concentration, of one or more prognostic marker (or biomarker) associated with the diagnosis and/or prognosis and/or therapeutic monitoring of metastatic cancer or recurrent cancer.

In a specific example, a method as described herein comprises qualitatively or quantitatively determining, analyzing or measuring a biological sample from a subject for the presence or absence, or amount or concentration, of one or more prognostic marker (or biomarker) associated with the diagnosis and/or prognosis and/or therapeutic monitoring of metastatic PTC or recurrent PTC.

The term "prognostic marker" or "biomarker" as used herein refers to a marker that informs about the outcome of a patient in the absence of systemic therapy or portends an outcome different from that of the patients without the marker, despite empiric (not targeted to the marker) systemic therapy.

The term "prognosis" as used herein, refers to the prediction of the likelihood of cancer-attributable death or progression, including recurrence, metastatic spread, and drug resistance, of a neoplastic disease, such as PTC.

The term "diagnosis" as used herein, refers to the identification of a molecular and/or pathological state, disease or condition, such as the identification of PTC, or other type of cancer.

The term "therapeutic monitoring" as used herein refers to the observation of the response of the subject to the treatment administered to it.

The determination, analysis or measurement of the biomarker is correlated with the benefit of treatment of PTC in the patient. In some examples, a patient sample is compared to a control sample. In some examples, a control is not used and qualitative or quantitative methods are used to determine the presence or absence, or amount or concentration of the protein of interest.

The term "sample" as used herein, encompasses a variety of cells, cell-containing bodily fluids and/or secretions as well as tissues including, but not limited to a cell(s), tissue, whole blood, blood-derived cells, plasma, serum, sputum, mucous, bodily discharge, and combinations thereof, and the like.

Methods of obtaining such samples from a subject are known to the skilled worker.

As used herein, "obtaining a sample" or "obtaining a biological sample" refers to such methods as will be well known to the skilled worker. A biological sample may be obtained directly or indirectly from the subject. The term "obtaining" a biological sample may comprise receiving a biological sample from an agent acting on behalf of the subject. For example, receiving a biological sample from a doctor, nurse, hospital, medical center, etc., either directly or indirectly, e.g. via a courier or postal service. In some cases the biological sample is obtained from archival repositories. In one example, the methods of the invention are carried out in vitro or ex vivo.

Means for enriching for cancer cells in a sample are known in the art. For example, the tissue may be isolated from paraffin or cryostat sections. Cancer cells may also be separated from normal cells by flow cytometry or laser capture microdissection. These, as well as other techniques for separating cancerous from normal cells, are known in the art.

In one example, and in the case of PTC, a sample is obtained using fine needle aspirate (FNA).

In one example, in determining whether there is strong, moderate or minimal (or absent) amount of the biomarker, the patient sample may be compared to one or more control samples. In one example, a control sample has had known and/or established level of the biomarker. In one example, a control sample is a patient sample that has known and/or established levels of biomarker expression and/or known clinical outcome. In one example, a control is a cell line that has a known amount of biomarker expression.

The term "expression", as used herein, and for example in reference to a biomarker such as PDGFR-α, refers to all indicators of transcriptional expression of the biomarker encoding gene. Such indicators include biomarker transcript products, generated as a result of transcription of the biomarker gene; translation products, including all forms of the biomarker protein, generated as a result of translation of the biomarker transcripts; and demonstrable or otherwise measurable biomarker activity.

As used herein, "biomarker protein", includes, but is not limited to, full-length proteins, mature proteins, pre-proteins, polypeptides, isoforms, mutations, variants, post-translationally modified proteins and variants thereof. Biomarker protein detection is know to the skilled worker, and is discussed herein.

Biomarker transcripts or mRNA can be measured using any of many techniques known to those of skill in the art, including, but not limited to, northern hybridization, PCR, reverse transcription followed by PCR, quantitative real-time PCR, nuclease protection assay, and in situ hybridization.

Biomarker activity can be measured by a variety of assays known to those of skill in the art. A suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Biomarker protein can be measured/detected by a variety of techniques known to the skilled worker, including, but not limited to, immunoassays using a biomarker specific antibody. Protein levels can also be determined using a specific antibody or mass spectroscopy in conjunction with 2 dimensional gel electrophoresis (separation of proteins by their isoelectric point (IEF) in the first dimension followed by molecular weight determination using sodium dodecyl sulphate polyacrylamide gel electrophoresis (SDS-PAGE)).

In other examples, a biomarker protein is detected using a binding agent including, but not limited to, a lectin, nucleic acid (e.g. DNA, RNA), monoclonal antibody, polyclonal antibody, Fab, Fab', single chain antibody, synthetic antibody, aptamer (DNA/RNA), peptoid, zDNA, peptide nucleic acid (PNA), locked nucleic acid (LNA), synthetic or naturally occurring chemical compound (including but not limited to a drug or labeling reagent), dendrimer, or any combination thereof. In some instances, a single agent is used to detect a biomarker. In other instances, a combination of different agents is used to detect a biomarker Detection includes direct and indirect detection. Similarly, a binding agent can be directly or indirectly labeled.

The quantity of one or more biomarkers can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server.

In some examples, qualitatively or quantitatively determining, analyzing or measuring a biological sample from a subject for the presence or absence, or amount or concentration, of one or more prognostic marker associated, is carried out using antibodies to the biomarker.

In a specific example, antibodies of the present invention are immunoreactive or immunospecific for, and therefore specifically and selectively bind to a biomarker, for example the protein PDGFRα. In one example, antibodies which are immunoreactive and immunospecific for PDGFRα can be used. Antibodies PDGFRα are preferably immunospecific.

The term "antibody" and "antibodies" includes, but is not limited to, monoclonal and polyclonal antibodies. Antibodies may be derived from multiple species. For example, antibodies include rodent (such as mouse and rat), rabbit, sheep, camel, chicken, and human antibodies. In another example, antigen binding fragments which specifically bind to PDGFRα are used. In some example, the antibodies also comprise a label.

The term "label" as used herein is an identifiable substance that is detectable in an assay and that can be attached to a molecule creating a labeled molecule. The behavior of the labeled molecule can then be monitored and/or studied and/or detected.

Examples of labels include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate. The particular label used will depend upon the type of immunoassay. Antibodies can be tagged with such labels by known methods.

The term "binds specifically" refers to high avidity and/or high affinity binding of an antibody to a specific polypeptide e.g., an epitope of PDGFR-α. Antibody binding to its epitope on this specific polypeptide is stronger than binding of the same antibody to any other epitope, particularly those which may be present in molecules in association with, or in the same sample, as the specific polypeptide of interest. Antibodies which bind specifically to a polypeptide of interest may be capable of binding other polypeptides at weak, yet detectable, level. Such weak binding, or background binding, is readily discernable from the specific antibody binding to the compound or polypeptide of interest, e.g., by use of appropriate controls, as would be known to the worker skilled in the art.

In one example, a sample containing cancerous cells or suspected as containing cancerous cells is obtained from the patient which is at risk for PTC, is suspected of having PTC, and/or has been diagnosed with PTC. Collection of such a sample is well known to the skilled worker. In a specific example, the sample is a fine needle aspirate (FNA) sample. Methods of obtaining a FNA sample, processing and/or storage of such a sample are also well known to the skilled worker. In other example, a sample is obtained from surgical dissection.

Tissue samples may be fresh-frozen and/or formalin-fixed, paraffin-embedded tissue blocks prepared for study by immunohistochemistry (IHC). In one example, the sample is a formalin fixed and/or paraffin-embedded tumor tissue from a biopsy or surgical resection of a cancer (e.g., tumour). Samples may also be processed by, snap freezing, treated to isolate DNA, RNA, or protein, or any combination.

The methods of the present invention may be accomplished using any suitable method or system of immunohistochemistry or quantifying levels of mRNA. Non limiting examples include automated systems, quantitative IHC, semi-quantitative IHC, RT-PCR and qRT-PCR and manual methods.

The term "quantitative" immunohistochemistry refers to an automated method of scanning and scoring samples that have undergone immunohistochemistry, to identify and quantitate the presence of a specified biomarker, such as an antigen or other protein. For example, to quantitate PDGFR-α, the score given to the sample is a numerical representation of the intensity of the immunohistochemical staining of the sample, and represents the amount of target biomarker present in the sample. As used herein, Optical Density (OD) is a numerical score that represents intensity of staining as well as the percentage of cells that are stained. As used herein, semi-quantitative immunohistochemistry refers to scoring of immunohistochemical results by human eye, where a trained operator ranks results numerically (e.g., as 0, 1 or 2).

In a specific example, expression of the biomarker in a sample is assessed by an operator as "2+" (denoting strong staining), "1+" (denoting moderate staining), or "0" (denoting minimal or absent staining). In some instance, each sample is assessed in duplicate, or triplicate. In another specific example, Nuclear staining is not scored and the correlations for staining were assessed using Fisher's exact test for tables and Spearman rank correlation for continuous variables.

In one example of the methods described herein, a biological sample from a subject is assessed for presence of a biomarker within the biological sample, wherein the levels and/or concentration of the biomarker indicates the aggressiveness or metastatic potential of PTC.

Automated sample processing, scanning and analysis systems suitable for use with immunohistochemistry are known in the art, and may be used with the methods described herein. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples.

In a specific example, the detection, analysis or measurement of PDGFR-α protein within a tissue sample is carried out using immunohistochemistry (IHC). It will be clear to the skilled worker that other immuno assays, both qualitative and quantitative, may be used in the present invention.

In one example, immunohistochemisty is carried out using tissue microarrays from formalin tissues.

Other examples that may be used in the detection, analysis or measurement of PDGFR-α include, but are not limited to, immunoprecipitation, immunoblotting, mass spectrometry, quantitative fluorescence activated cell sorting, enzyme linked immunosorbent assay, immunohistochemistry, quantitative immunohistochemistry, fluorescence resonance energy transfer, Forster resonance energy transfer, and biomolecular fluorescence complementation.

In determining whether there is strong (e.g., 2+) or moderate (e.g., 1+) or minimal (e.g., 0) PDGFR-α staining, the patient sample may be compared to one or more control samples. In one example, a control sample is a patient sample that has known and/or established levels of PDGFR-α tumour staining and/or known clinical outcome. In one example, a control is a cell line that has a known amount of PDGFR-α staining.

In some example, a control is not used and qualitative or quantitative methods are used to determine the level of staining.

In practice, in the example in which a patient sample is determined to have moderate (1+) or strong (2+) expression (i.e., strong expression of PDGFR-α), the patient is identified as a subject with an increased likelihood of developing or having metastatic papillary thyroid cancer (PTC), or a subject with an increased likelihood of developing or having recurrent PTC, and so is considered a good candidate for, and subjected to treatment comprising, surgical resection and/or radio therapy (such as radio iodine ablative therapy or external beam radiotherapy), and/or chemotherapy.

In practice, in the example in which a patient sample is determined to have minimal staining ("0") expression (e.g., absent or minimal expression of PDGFR-α), the patient is identified as a subject not having an increased likelihood of developing or having metastatic papillary thyroid cancer (PTC), or a subject not having an increased likelihood of developing or having recurrent PTC. Continued treatment options for such patients identified as not having a likelihood of developing or having metastatic or recurrent are known to the skilled worker. For example, patients lacking confirmed metastases from PTC in many cases do not get radioactive iodine, but this depends on the size of the primary tumor. Regardless of their initial treatment including surgery and/or radioactive iodine all patients are followed with serial imaging including whole body iodine scans, neck ultrasound and serum thyroglobulin assessments on a yearly basis essentially for the rest of their life although the interval between follow-up visits decreases from six months initially for approximately 2 years to yearly after that. Metastases from thyroid cancer typically occur within 2 to 3 years that can come back as late as 10 or 15 years after their original surgery and treatment.

In a specific example, in the case of examined PDGFR-α and β expression in a tissue array of papillary thyroid cancer including primary tumor specimens with (n=58) and without (n=66) nodal metastases, for PDGFRα, in primary tumors without lymphatic metastases, a small fraction of the tumors were positive (16%) but most of the staining was moderate at 1+ (Table 2). However, in primary tumors with lymph node metastases the majority (83%) of the tumors were positive for PDGFRα expression (p=0.003). Nodal deposits in all but one case are positive for PDGFR-α with most cases exhibiting strong staining (Table 2). PDGFR-β staining in primary tumor specimens demonstrated significantly different results. PDGFR-β staining did not follow a pattern with respect to the absence or presence of nodal metastases. Approximately 90% of all tumors, a nearly equal fraction of lymph node negative and lymph node positive cases, stained for PDGFR-β and staining qualitatively was also very similar (p=0.82) (see Table 2).

Figure 2:
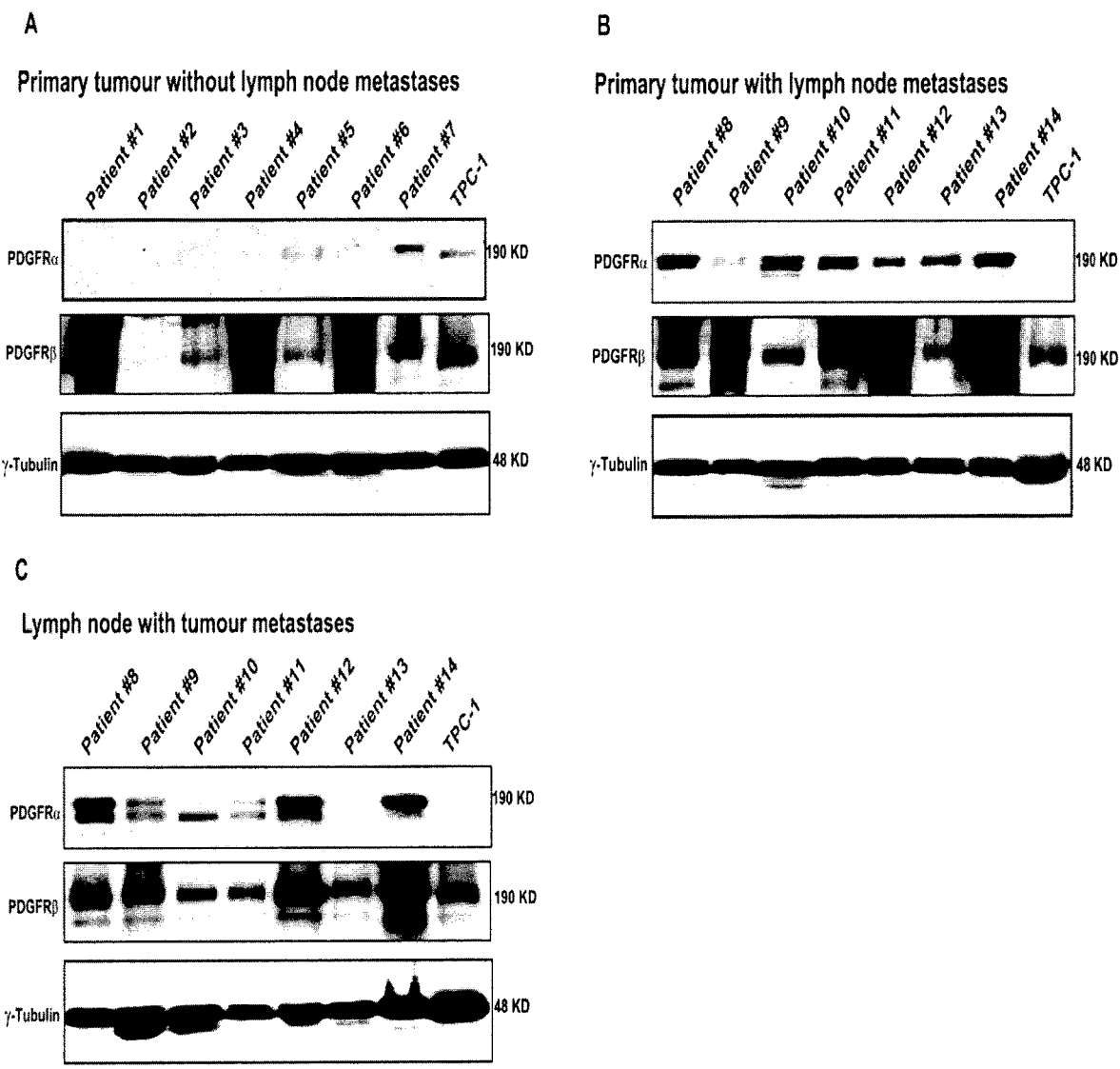
FIGS. 2A-2C show Western blots of PDGFR-α and -β in patient primary tumors lacking nodal metastases (#1-7, far left) (FIG. 2A) compared to those with nodal metastases (#8-14, middle section) (FIG. 2B), corresponding metastatic disease deposits from patients #8-14 are shown in the far right section (FIG. 2C)

In another specific example, in the case of freshly prepared PTC tumour isolated at operative resection, with and without nodal metastases, PDGFR (α and β) configuration and nodal involvement was determined in 14 cases that included level 6 lymph node dissections as shown in FIG. 2. Only 2 of 7 primary tumors without nodal metastases expressed PDGFR-α (patient #5 and #7). In fact the only clearly positive result expressing PDGFR-α (patient #7) was a false positive due to an unexpected case of sarcoidosis with fibrotic reactions in all of the nodes removed as documented clearly on pathology.[47,48] In 7 of 7 primary tumors with nodal metastases we observe PDGFR-α expression. Even if we include the likely false positive (patient #7) and the very weak staining in patient #5, the difference in number of positive cases for PDGFR-α between node− (2/7) and node+ (7/7) cases is significant (P=0.02). All of the nodal metastases examined express PDGFR-α although the levels vary significantly (FIG. 2).

It will be appreciated that in some circumstances, a patient which is initially identified a not having an increased likelihood of developing or having metastatic PTC or recurrent PTC, may relapse or reoccur. Such a reoccurrence can manifest is several ways, including but not limited to, reoccurrence of the primary tumour and development of metastasis. In addition to, or alternatively, an additional distinct tumour can arise. The methods as described herein may be used in the therapeutic monitoring of a patient, to monitor and identify those patients which may relapse.

In accordance with one aspect of the present invention, there is provided a method comprising: a) obtaining a sample from a subject with, or suspected as having, PTC; b) contacting the sample with an antibody to a biomarker, to form a complex between the antibody and the biomarker present in the sample; c) measuring the complex formed to determine the amount or concentration of said biomarker in the sample; wherein the determination of a benefit for treatment is determined by a strong expression of the biomarker in the sample. In one example, the biomarker is PDGFRα. In one example, expression of the biomarker in the sample is compared to a control. In one example, said sample comprises a FNA sample.

In another embodiment, PDGFRα expression is associated with the development of metastasis in a patient with PTC.

In accordance with another aspect of the present invention, there is provided a method comprising: a) obtaining a sample from a subject with, or suspected as having, PTC; b) processing said sample, c) contacting the processed sample with an analyte or reagent to a biomarker, to form a complex between the analyte or reagent and the biomarker present in the processed sample; c) measuring the complex formed to determine the amount or concentration of said biomarker in the sample; wherein the determination of a benefit for treatment is determined by a high amount or concentration (or strong expression) of the biomarker in the sample. In one example, the biomarker is PDGFRα. In one example, expression of the biomarker in the sample is compared to a control. In one example, said sample comprises a FNA sample. In another embodiment, PDGFRα is associated with the development of metastasis in a patient with PTC.

There is further provide the step of treating a subject with a high concentration or amount (or strong expression) of PDGFRα with a treatment for PTC.

In some examples, processing said sample permits analysis of the biomarker within the sample. In some example, processing refers to isolating or extracting biomarker transcript from said sample, said RNA suitable for analysis. In some examples, processing refers to isolating of extracting biomarker protein from said sample, said protein suitable for subsequent analysis.

Analysis includes, but is not limited to, performing an analyte assay with said processed sample. For example, performing an analyte binding assay configured to detect a biomarker in said processed tumor sample by introducing the processed tumor sample into an assay instrument which (i) contacts a reagent which specifically binds for detection of the biomarker within the tumor sample, and (ii) generates one or more assay results indicative of binding of said biomarker. As noted herein, said biomarker is a biomarker protein, a biomarker transcript, or biomarker activity.

In some examples, the analyte binding assay in an immunoassays. In some examples, said immunoassay is immunohistochemistry. In some example said immunohistochemistry is performed with an automated system, or a manual system.

In some example, the analyte binding assay comprises detecting said biomarker RNA, include but limited to, using RT-PCT or in situ hybridization.

The assay results may be quantitative or semi-quantitative.

Additional specific examples of processing comprises formalin fixing, or paraffin-embedding, or both formalin fixing and paraffin-embedding, said sample.

Treatment of said subject may comprise surgical resection of thyroid and lymph nodes, radio therapy, chemotherapy, or combinations thereof. Radio therapy comprises radio iodine ablative therapy or external beam radiotherapy. Chemotherapy comprises a tyrosine kinase inhibitor such as sorafenib, sunitinib, axitinib, or motisanib.

Treatment of said subject may comprise surgical resection of thyroid and lymph nodes, radio therapy, chemotherapy, or combinations thereof. Radio therapy comprises radio iodine ablative therapy or external beam radiotherapy. Chemotherapy comprises a tyrosine kinase inhibitor such as sorafenib, sunitinib, axitinib, or motisanib.

The methods described herein are useful in the modulation of PTC progression.

As used herein, the term "modulation of PTC progression" refers to the ability of a compound to increase or decrease the likelihood that a PTC will progress to an aggressive prostate cancer and/or will metastasize. Generally, compounds therapeutically useful are those that decrease the likelihood of PTC progression.

Accordingly, in one example, a subject identified with a likelihood of developing or having metastatic PTC is treated so as to modulated PTC progression, and in particular to decrease the likelihood of PTC progression. In one example, inhibition of PDGFRα reduces the likelihood of a patient with PTC developing metastases. In a specific example, a subject identified with a likelihood of developing or having metastatic PTC is treated with an inhibitor of PDGFRα.

There is provided a method for the treatment of a subject with a likelihood of developing or having metastatic PTC, comprising administering to said subject an inhibitor of PDGFRα.

Inhibitors of PDGFRα include, but are not limited to, RNA interference molecules, small molecules, nucleic acids, antibodies, peptides, pharmaceutical compositions, and/or aptamers.

Examples of RNA interference molecules include a RNAi molecule, a siRNA molecule, or a shRNA molecule.

The term siRNA (short interfering RNA) or siRNA duplexes, as used herein has the same meaning as typically in the art. i.e. the term siRNA refers to double stranded RNA complex. Often, the complex has 3'-overhangs. In one example, siRNA are commercially available.

Pharmaceutical compositions include, but are not limited to, sorafenib, sunitinib, axitinib, or motisanib.

Pharmaceutical compositions include, but are not limited to, sorafenib, sunitinib, axitinib, or motesanib.

Methods of the present invention are conveniently practiced in the form of a kit. Such a kit preferably contains antibodies for PDGFRα and instructions for the use thereof. In a specific example, the kit further comprises at least one control sample for PDGFRα.

As described herein, there is provided a kit for identifying a subject with an increased likelihood of developing or having metastatic papillary thyroid cancer (PTC), or a subject with an increased likelihood of developing or having recurrent PTC, comprising: a) instructions for determining the amount of PDGFRα in a sample from said patient; b) a reagent for measuring the amount PDGFRα in said sample, wherein in the case in which said patient sample is determined to have "2+" or strong expression (i.e., strong expression of PDGFR-α), said patient is identified as a subject with an increased likelihood of developing or having metastatic papillary thyroid cancer (PTC), or a subject with an increased likelihood of developing or having recurrent PTC.

In one example, said reagent is an antibody to PDGFRα. In one example positive and/or negative control samples are also included in the kit.

As described herein, there is provided systems for treating a subject with or suspected of having papillary thyroid cancer, comprising: a) a reagent which specifically binds for detection of PDGFR-α in a tumor sample from a patient with thyroid cancer, and b) an assay instrument configured to receive a tumor sample and contact the reagent with the tumor sample, and to generate one or more assay result indicative of binding said reagent with the PDGRF-α within the tumor sample which is assayed for specific binding.

To gain a better understanding of the invention described herein, the following examples are set forth. It should be understood that these examples are for illustrative purposes only. Therefore, they should not limit the scope of this invention in anyway.

EXAMPLES

Example I

Patients and Methods
Patient Specimens

Ethics approval was obtained through the University of Alberta Heath Research Ethics Board ID Pro00018758. Specimens prepared for primary cell culture were placed in culture media within 10 minutes of devascularisation. For tissue banking specimens were placed in OCT (Optimal Cutting Temperature compound) within 20 minutes of devascularisation and snap frozen in liquid $N_2$. For the tissue array with paraffin specimens, a total of 124 patients were selected with papillary thyroid carcinoma, 66 without and 58 with lymphatic metastases. In all cases patients had a total thyroidectomy with a level VI lymph node dissection such that histopathology could be used to document the true node negative cases that complemented our clinical assessment via ultrasound. Both primary tumor specimens and matching nodal metastases were available in 13 cases. Cases included were all papillary thyroid carcinoma in the absence of any aggressive variants such as insular or tall cell papillary thyroid cancer. Two pathologists separately assessed the specimens to document primary tissue diagnosis as well as the presence of lymphatic metastases in nodes sectioned.

Immunohistochemistry

Immunohistochemistry was performed using standard techniques. Briefly, formalin-fixed, paraffin-embedded tissue sections of 4 µM thickness were deparaffinized and rehydrated. The antibodies used for the Western blots and for staining the paraffin tissue arrays as follows: antibodies against Akt, phospho-Akt (Ser473), PDGFR-α, phospho-PDGFR-α/β (Tyr849)/β (Tyr857), p44/42MAPK/ERK, and phospho-p44/42 MAPK/ERK (Thr202/Tyr204) were all purchased from Cell Signalling Technology (Danvers, Mass., USA). The PDGFR-β antibody was purchased from Santa Cruz Biotechnology, (Santa Cruz, USA). Heat-induced epitope retrieval was performed using citrate buffer (pH 6.0) and pressure cooked in a microwave for 20 minutes. The endogenous peroxidase activity was blocked using 3% $H_2O_2$ in methanol for 10 minutes. Tissue sections were then incubated with The PDGFR-α and -β overnight at 4° C. in a humidified chamber. After 2 washes with PBS, tissue slides were incubated with biotinylated linked universal secondary antibody and subsequently with streptavidin-HRP complex as per the manufacturer's instructions (LSAB+ system, Dako). Tissue sections were incubated with 3,3'-diaminobenzidine/$H_2O_2$ (Dako) for color development and counter-stained with hematoxylin.

Marker Scoring and Statistical Analysis

Evaluation of immunostaining was performed without knowing the clinical outcome and the other staining results. The cytoplasmic expression of PDGFR-α and PDGFR-β was assessed for each case, in triplicate, as 2+ (strong staining), 1+ (moderate staining), 0 (minimal staining). Nuclear staining was found in all specimens and not scored. The correlations for staining were assessed using Fisher's exact test for tables and Spearman rank correlation for continuous variables. Sample cores on the tissue array that were fragmented or incomplete were not scored.

Cell Culture

TPC-1, KTC-1, BCPAP experimental cell lines were all generously provided by Dr. Ezzat, University of Toronto. 8305C was purchased from DSMZ (Braunschweig, Germany). RET/PTC, BRAF and RAS mutation status as outlined in Table 1 and cell origin confirmed using Pax-8 and TTF-1 staining (Table 1).[45] RPMI 1640 was purchased from Life Technologies (Grand Island, N.Y.). Standard fetal bovine serum (FBS) was purchased from Hyclone (Logan, Utah, USA). Trypsin-EDTA containing 0.25% trypsin, and PDGF-BB were purchased from GIBCO (Invitrogen, Grand Island, N.Y., USA). Sunitinib malate was purchased from TORCIS Bioscience (Ellisville Mo. USA).

Primary cell culture and experimental cell lines were maintained in RPMI 1640 media supplemented with 10% FBS. The cells were seeded in a 100-mm culture dish and were grown in a humidified 5% $CO_2$ incubator. For PDGF-BB stimulation (25 ng/ml), cells were grown to about 80% confluence and incubated in serum-free medium overnight prior to each experiment. MAP1C/ERK inhibitors U0126 and PD98059 were purchased from Calbiochem (Toronto, Ontario, Canada). PI3K/Akt inhibitor Ly294002 was purchased from Cell Signaling Technology (Danvers, Mass., USA). Cells that were treated with inhibitors were given varying concentrations: U0126; 2 umol/L and 10 umol/L; Ly294002 10 umol/L and 25 umol/L; Sunitinib 0.25 umol/L. In all cases, unless otherwise indicated the inhibitors were given to cells and 60 minutes later the PDGF-BB was added to the cultures followed by Western blot analysis.

Western Blot Analyses

Cells were lysed in RIPA buffer [150 mM NaCl, 100 mM Tris (pH 8.0), 1% Triton X-100, 1% deoxycholic acid, 0.1% SDS, 5 mM EDTA, and 10 mM NaF] supplemented with 1 mM sodium vanadate, 2 mM leupeptin, 2 mM aprotinin, 1 mM phenylmethylsulfonyl fluoride (PMSF), 1 mM DTT, 2 mM pepstatin, and 1:100 protease inhibitor cocktail set III on ice. After centrifugation at 4° C. at 18,000 rpf for 15 mM, the supernatant was harvested as the total cellular protein extracts and stored at −80° C. The protein concentration was determined using Bio-Rad protein assay reagent (Richmond, Va., USA). Running samples were prepared by adding a sample reducing agent and SDS sample buffer, incubating at 98° C. for 5 min. Aliquots of protein extract samples were separated by SDS-polyacrylamide gel electrophoresis (SDS-PAGE) and transferred to nitrocellulose membrane. Membranes were blocked with 5% nonfat dry milk in 1×TBS containing 0.05% Tween-20 for 60 min, followed by incubation with primary antibodies 4° C. overnight. Protein bands were detected by incubation with horseradish peroxidase-conjugated antibodies (Pierce Biotechnology, Rockford, Ill., USA) and visualized with SuperSignal West Pico chemiluminescence substrate (Thermo Scientific, Rockford, Ill., USA).

Short Interfering RNA (siRNA) and Transfections siRNA for PDGFR-α and scrambled siRNA were purchased from Siegen (Foster, Calif., USA). Transient transfections of TCP-1, 8305C cells (3×10⁶ cells) were performed using the Electro square electroporator BTX ECM 800 (225V, 8.5 ms, 3 pulses). 1 nmol/L of siRNA or scrambled control was used 3 million of TPC-1 and 8305C cells. The efficiency of target gene inhibition was assessed after 48 hours transfection by using Western blotting.

Transwell Migration/Invasion and Cell Growth Assays

As previously described, Cytoselect™ 96-well cell invasion assay kit was used (Cell Biolabs, San Diego, Calif., USA) to assess cell invasiveness according to the manufacturer's protocol.[46] Briefly, TPC-1, BCPAP and 8305C after transfected with either PDGFRα siRNA or scramble siRNA, 10000 cells were starved overnight and added to the inserts, PDGF-BB was added to some wells at the concentration of 25 ng/mL, PDGF-BB was added 1 h later for inhibitors, sunitinib (0.2 umol/L), Ly294002 (10 umol/L) and (U0126) 2 umol/L, cells were seeded into the insert plate for 16 hours, the invasive cells passed through basement membrane layer to the bottom and dissociated from membrane by the addition of cells detachment buffer, the invasive cells were lysed and followed by quantification using CyQuant OR fluorescent Dye. For cell viability analysis 10000 cells were seeded per well and cultured for 16 hours. MTS assay (Promega, Madison, USA) was then performed in 4 replicates followed manufacturer's instructions. PTC cell lines transfected with PDGFR specific siRNA or scrambled control were plated at a density of 10,000 or 20,000/ml and cultured for 5 days. Cell counts were done on days 2, 3 and 5 using trypan blue (Sigma-Aldrich, Oakville, Canada) and results expressed as total number of viable cells. MTS assay was done in 7 replicates as per manufacturer's instructions. The absorbance was recorded by a BioRad spectrophotometer at day 5 of cell culture.

Statistical Analysis

Data were expressed as the mean±S.E. from a minimum of three independent experiments. Statistical analyses were performed with a completely random design one-way ANOVA. The correlations between PDGFR and the other biological markers were assessed using Fisher's exact test for tables and Spearman rank correlation for continuous variables. Statistical tests are two-tailed with a P value <0.05 considered to be statistically significant. The SAS computer program SAS (r) 9.2 (TS1M0) was used to perform the analysis Results PDGFR-α Expression, but not PDGFR-β, is Associated with Lymphatic Metastases in Papillary Thyroid Cancer We examined PDGFR-α and β expression in a tissue array of papillary thyroid cancer including primary tumor specimens with (n=58) and without (n=66) nodal metastases with representative sections shown in FIG. 1. FIG. 1 shows representative immunohistochemical stains of PDGFR-α in papillary thyroid cancer (PTC) primary tumors without nodal metastases at low power (A) (100×) and high power (B) (400×). Primary tumors with nodal metastases are shown (C) (100×) and (D) (400×). Cytoplasmic staining demonstrates much higher levels of PDGFR-α in node-positive (C and D) primary tumor specimens as opposed to node-negative specimens (A and B).

All patients had a level 6 lymph node dissection to best assess the possibility of lymphatic metastases. Included in the array were neighboring, normal thyroid tissue cores (n=32) and matching nodal thyroid cancer metastases from 13 primary tumors. For PDGFR-α, in primary tumors without lymphatic metastases, a small fraction of the tumors were positive (16%) but most of the staining was weak at 1+ (Table 2). However, in primary tumors with lymph node metastases the majority (83%) of the tumors were positive for PDGFR-α expression (p=0.003) (Table 2). Moreover, nodal deposits in all but one case are positive for PDGFR-α with most cases exhibiting strong staining (Table 2). PDGFR-β staining in primary tumor specimens demonstrated significantly different results. PDGFR-β staining did not follow a pattern with respect to the absence or presence of nodal metastases. Approximately 90% of all tumors, a nearly equal fraction of lymph node negative and lymph node positive cases, stained for PDGFR-α and staining qualitatively was also very similar (p=0.82) (see Table 2). Nodal metastases also commonly expressed PDGFR-β (>90%). Expression of PDGFR-α and -β was undetectable in most (95%+) of the non-neoplastic, normal thyroid tissue (Table 2).

TABLE 2

Percentage (%) of specimens staining for PDGFR-α and -β in normal thyroid, papillary thyroid cancer primary tumors and nodal metastases.

| Stain | Scoring | | 0 | 1+ | 2+ |
|---|---|---|---|---|---|
| PDGFR-α | benign thyroid | (n = 35) | 97 | 3 | 0 |
| | node negative primary | (n = 66) | 84 | 12 | 4 |
| | node positive primary | (n = 58) | 17 | 39 | 44 |
| | lymph node metastasis | (n = 13) | 8 | 23 | 69 |
| PDGFR-β | benign thyroid | (n = 35) | 94 | 6 | 0 |
| | node negative primary | (n = 66) | 13 | 30 | 57 |
| | node positive primary | (n = 58) | 11 | 42 | 47 |
| | lymph node metastasis | (n = 13) | 8 | 8 | 84 |

To further assess differences in PDGFR-α and -β expression, we examined a cohort of freshly prepared PTC tumors isolated at operative resection, with and without nodal metastases. PDGFR (α and β) configuration and nodal involvement was determined in 14 cases that included level 6 lymph node dissections as shown in FIG. 2.

FIG. 2 shows Western blots of PDGFR-α and -β in patient primary tumors lacking nodal metastases (#1-7, far left) compared to those with nodal metastases (#8-14, middle section). Corresponding metastatic disease deposits from patients #8-14 are shown in the far right section. PDGFR-α is expressed primarily in primary tumors with metastatic disease and corresponding metastatic deposits (P=0.007). In contrast, PDGFR-β status does not correlate with metastatic disease. Patient #7 has sarcoidosis which induces nodal proliferation and is a benign cause for increased levels of PDGFR-α. The analysis was completed in all cases from freshly prepared tumor specimens. TPC-1 included as an internal control.

Only 2 of 7 primary tumors without nodal metastases expressed PDGFR-α (patient #5 and #7). In fact the only clearly positive result expressing PDGFR-α (patient #7) was a false positive due to an unexpected case of sarcoidosis with fibrotic reactions in all of the nodes removed as documented clearly on pathology.[47,48] In 7 of 7 primary tumors with nodal metastases we observe PDGFR-α expression. Even if we include the likely false positive (patient #7) and the very weak staining in patient #5, the difference in number of positive cases for PDGFR-α between node− (2/7) and node+ (7/7) cases is significant (P=0.02). All of the nodal metastases examined express PDGFR-α although the levels vary significantly (FIG. 2). Similar to what we observed in the tissue array, PDGFR-β expression does not appear to be linked to metastases in this patient cohort (FIG. 2). All but one of the specimens (patient #2) exhibited PDGFR-β staining but again the levels vary significantly between cases.

PDGFR-α Activation is Associated with MAPK/ERK and PI3K/Akt Signaling Pathways

Current models for receptor tyrosine kinase signalling involve both the MAPK/ERK and PI3K/Akt pathways.[39] To assess the role of each of these signal transduction pathways in metastatic PTC, we used primary cell culture to examine MAPK/ERK and PI3K/Akt activation in PTC metastatic tumour specimens.

Figure 3:
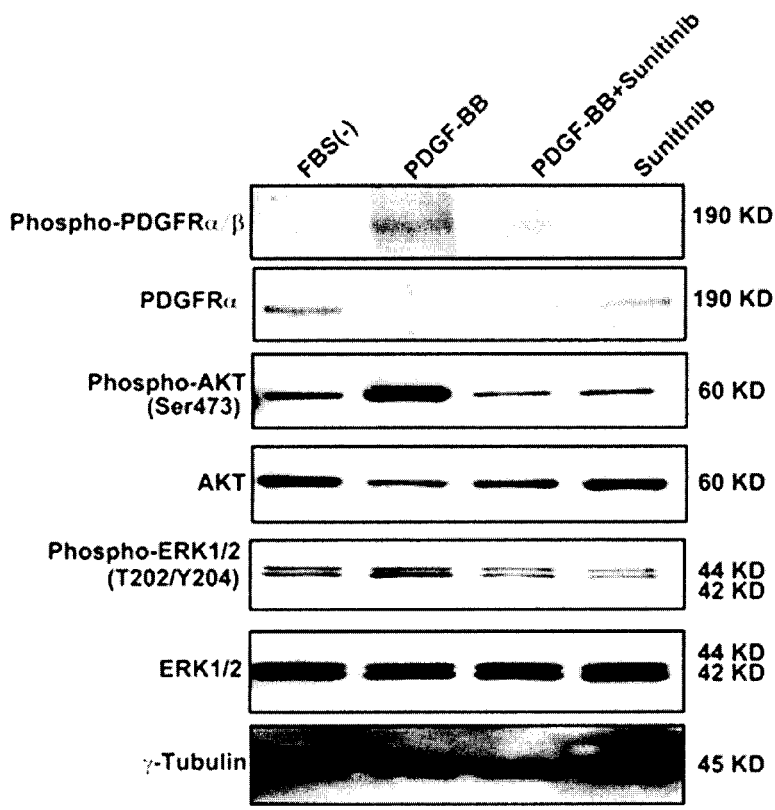
FIG. 3 shows Western blots of primary cell culture obtained from a lymph node specimen with metastatic papillary thyroid cancer confirmed by histology.

FIG. 3 shows Western blot of primary cell culture obtained from a lymph node specimen with metastatic papillary thyroid cancer confirmed by histology. The results show activated PDGFR-α (phospho-PDGFR) when stimulated with PDGF-BB with concomitant activation of the PI3K/Akt pathway as demonstrated by increasing levels of phospho-Akt. The stimulatory effect can be blocked by sunitinib, a tyrosine kinase inhibitor. Activation of the MAPK/ERK pathway (phospho-ERK) is present but to a much smaller degree in this semi-quantitative experiment.

Shown in FIG. 3 is a primary cell cultures of PTC metastatic tumour stimulated PDGF-BB with and without sunitinib to assess the effect of TKI therapy on PDGFR activation and downstream signaling. We observed significant increases in phospho-Akt, consistent with activation of the PI3K/Akt pathway and a small increase in phospho-ERK (MAPK/ERK pathway) with PDGF-138 stimulation of these cultured tumor cells (FIG. 3). Activation of both pathways was completed blocked with the addition of multikinase inhibitor sunitinib. Having demonstrated the concept that both pathways may be activated in metastatic PTC, we examined the status of both the MAPK/ERK and PI3K/Akt pathways in the 14 patients previously screened for PDGFR-α and -β.

Figure 4:
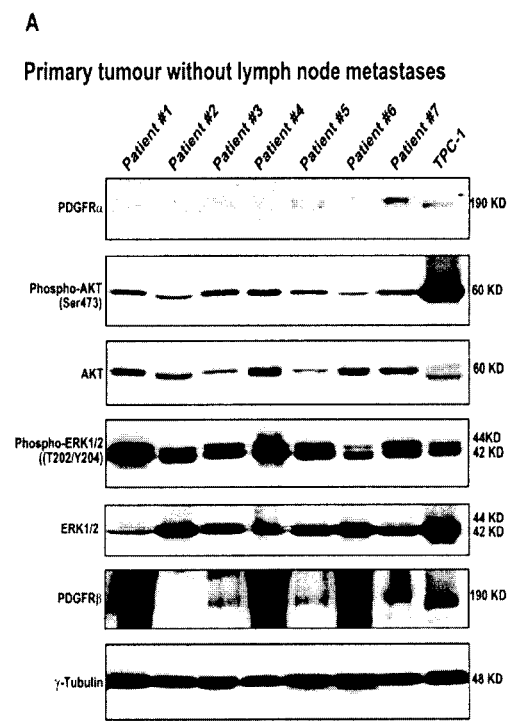
FIGS. 4A-4C show Western blots documenting the activation status of the MAPK/ERK and PI3K/Akt pathways in primary tumours lacking nodal metastases (#1-7, far left) (FIG. 4A) and those with nodal metastases (#8-14, middle section) (FIG. 4B), and corresponding metastatic disease deposits from patients #8-14 are shown in the far right section (FIG. 4C)
Figure 4:
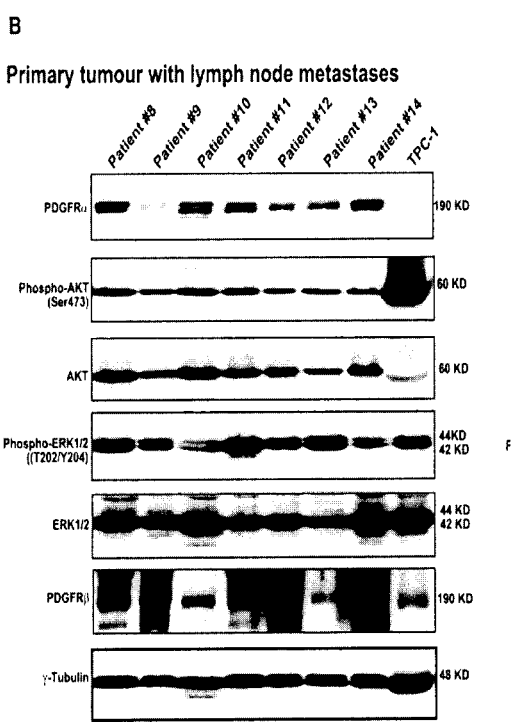
Figure 4:
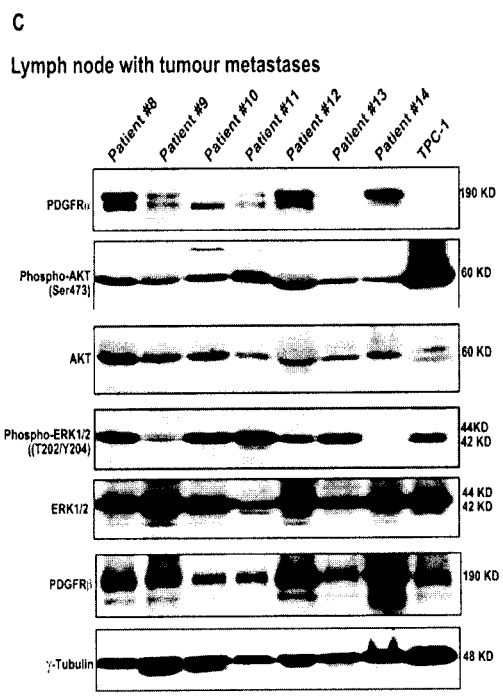

In FIG. 4, Western blots show the activation status of the MAPK/ERK and PI3K/Akt pathways in primary tumours lacking nodal metastases (#1-7, far left) and those with nodal metastases (#8-14, middle section). Corresponding metastatic disease deposits from patients #8-14 are shown in the far right section. The analysis was completed in all cases from freshly prepared tumour specimens. TPC-1 cell line used internal control for the different membranes.

Shown in FIG. 4 is a representative Western blot documenting activation of both the MAPK/ERK and PI3K/Akt pathways in all of the PTC primary tumors, with and without metastases. Typically we observed that both pathways are operative although in one case (patient #14) activation of the MAPK/ERK pathway was minimal.

PDGFR-α Activation Increases Invasive Potential in PTC Cell Lines and can be Blocked with Tyrosine Kinase Inhibitors Having demonstrated a strong correlation between PDGFR-α and nodal metastases in clinical specimens, PTC experimental cell lines were surveyed for differences in PDGFR receptor expression. We show here that there is a differential expression of PDGFR subtypes depending on the cell line (FIG. 5).

Figure 5:
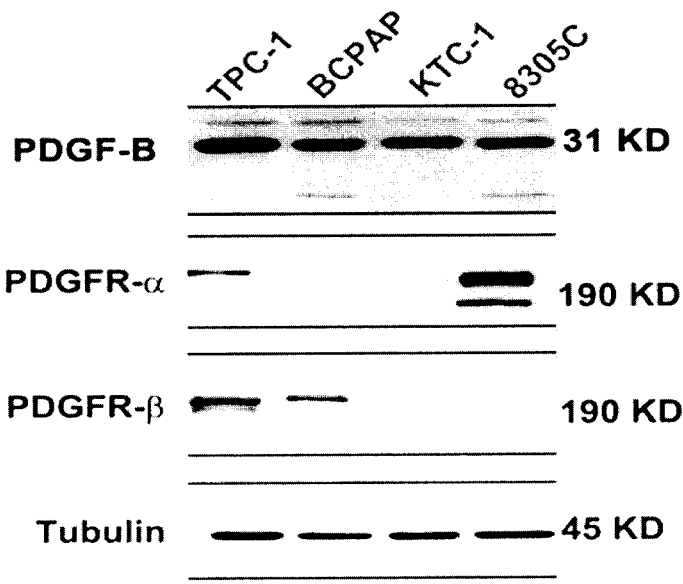
FIG. 5 shows Western blots of PDGFR configuration in the papillary thyroid cancer cell lines.

In FIG. 5, Western blot of PDGFR configuration in the papillary thyroid cancer cell lines is shown. TPC-1 is the only cell line with both alpha and beta subunits of PDGFR. The KTC-1 cell line represents an important naïve control for our experimental series. All cell lines express PDGF-BB ligand. Cell line integrity and origin was confirmed using thyroid-specific markers Pax-8 and TTF-1 (Table 1).

TPC-1 has both PDGFR-α and -β receptor isoforms, BCPAP has only PDGFR-β, 8305C only exhibits PDGFR-α and the KTC-1 cell line does not have either subunit. Using the Cytoselect™ invasion assay and in the presence of PDGFR ligand PDGF-BB, known to bind all subunits of PDGFR, we demonstrate significant differences in invasion potential of the cell lines depending on the configuration of the PDGFR. We also examined the effect of TKI blockade on invasive potential in these cell lines. In PTC-1 and 8305C, two cell lines with PDGFR-α, PDGF-BB stimulation lead to a significant increase in invasive potential (FIG. 6).

Figure 6:
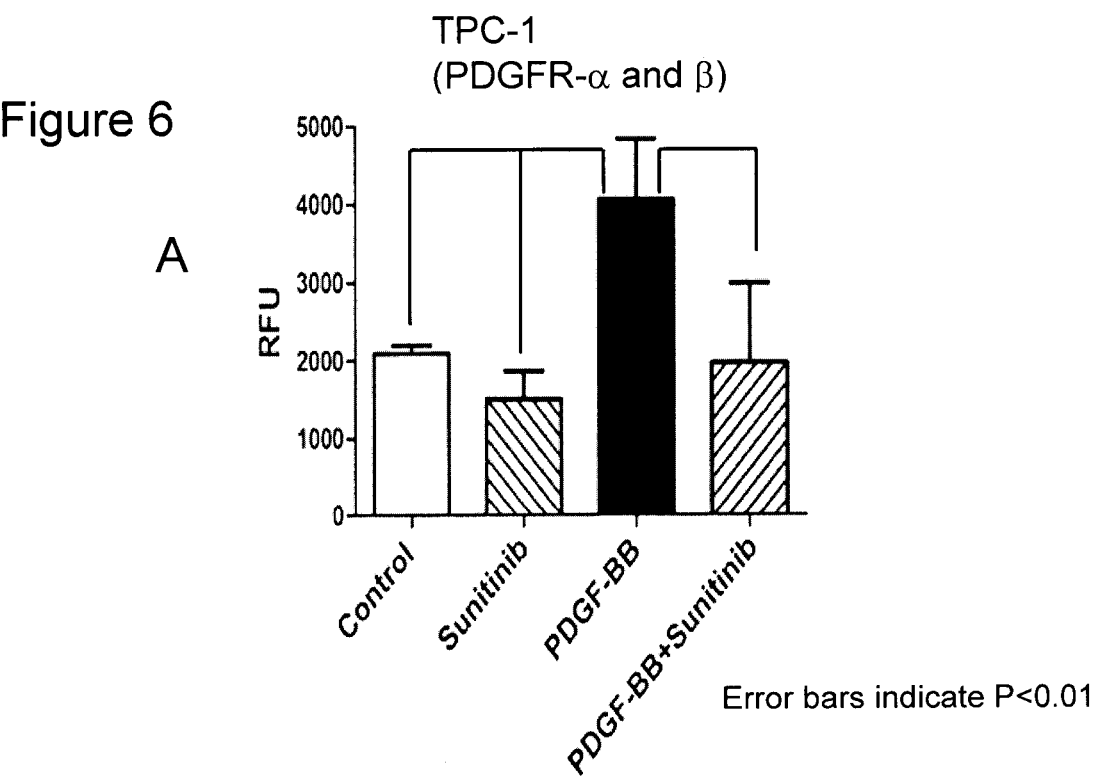
FIG. 6 shows Cytoselect assay results (in triplicate) for invasive potential of TPC-1 (A), 8305C (B), and BCPAP (C) cell lines.
Figure 6:
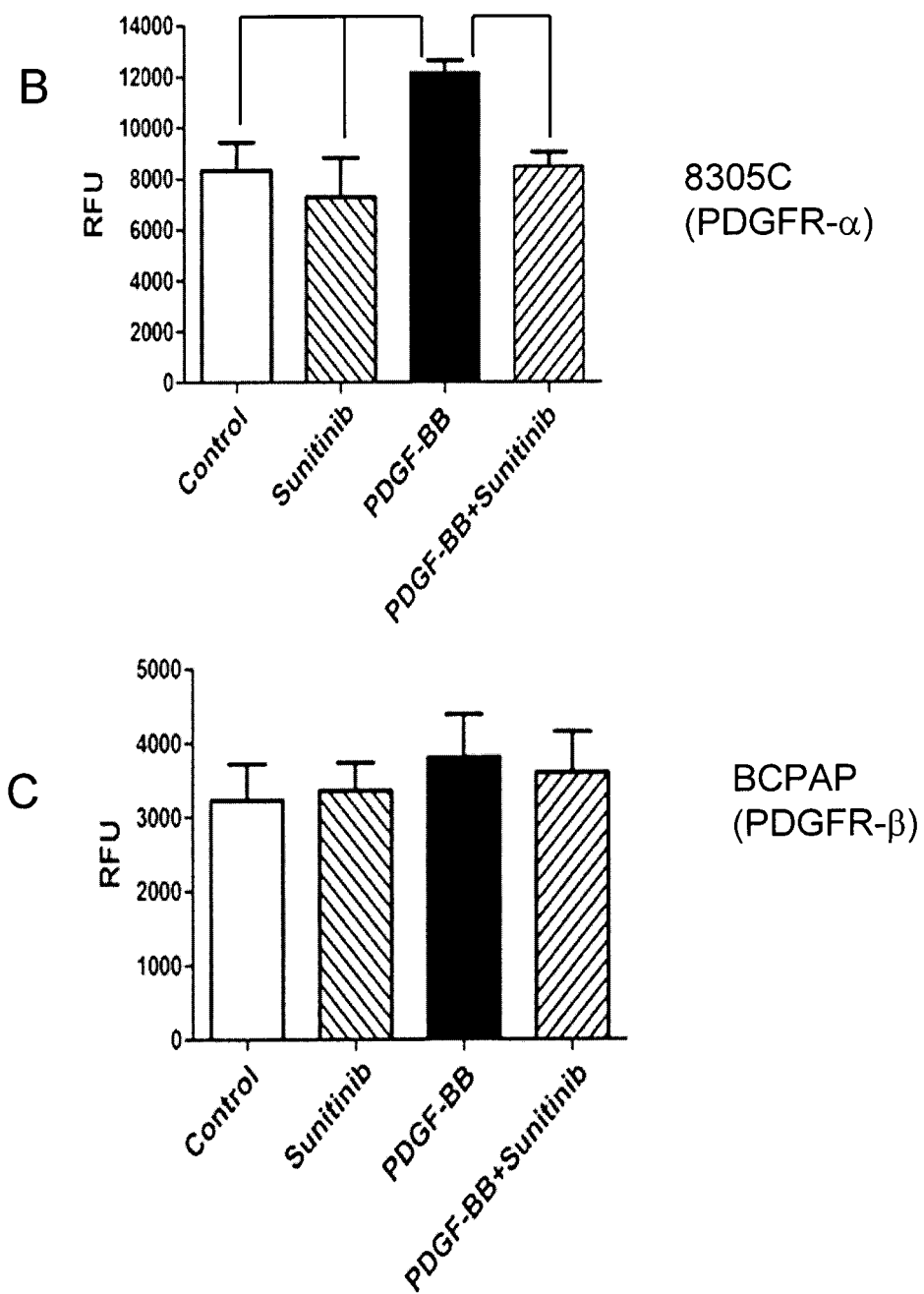

Cytoselect assay results (in triplicate) for invasive potential of TPC-1 (A), 8305C (B), and BCPAP (C) cell lines as shown in FIG. 6. The cell lines with the PDGFR-α subunit (TPC-1 and 8305C) demonstrated increased invasive potential with PDGF-BB stimulation, but not the BCPAP line which has only PDGFR-β. Sunitinib virtually completely abates any change in invasive potential with PDGF-BB stimulation of PDGFR. Sunitinib does not alter invasive potential without PDGF-BB stimulation in any of the cell lines.

The addition of sunitinib, a multikinase inhibitor, abated any change in invasive potential as a result of PDGF-BB stimulation for both cell lines (FIG. 6). Conversely, the BCPAP cell line (PDGFR-β only) did not exhibit any change in invasive potential (FIG. 6). The effect of sunitinib on cell growth for all of the cell lines in the absence of PDGF-BB stimulation was not significant (FIG. 6). KTC-1 also did not exhibit any change in invasive potential with PDGF-BB stimulation and increasing levels of PDGF-BB or longer periods of stimulation did not alter these results (not shown).

Selective Knockdown of PDGFR-α with siRNA Disrupts Invasive Potential

We used siRNA to disrupt expression of PDGFR-α and examined the subsequent effect on the invasive potential of cell lines exhibiting PDGFR-α and -β (TPC-1) or only PDGFR-α (8305C).

Cytoselect invasion assays with or without PDGFR-α siRNA for TPC-1 cell line (A) with corresponding cell viability assessment (B) are shown in FIG. 7. Invasion assays for 8305C cell line with PDGFR-α siRNA shown in (C) with corresponding cell viability experiment (D). The results strongly suggest that the PDGFR-α, but not -β, is essential to mediating increased invasive potential. siRNA significantly reduces PDGFR-α expression as shown in the accompanying Western blot. RFU refers to relative fluorescence units.

Figure 7A:
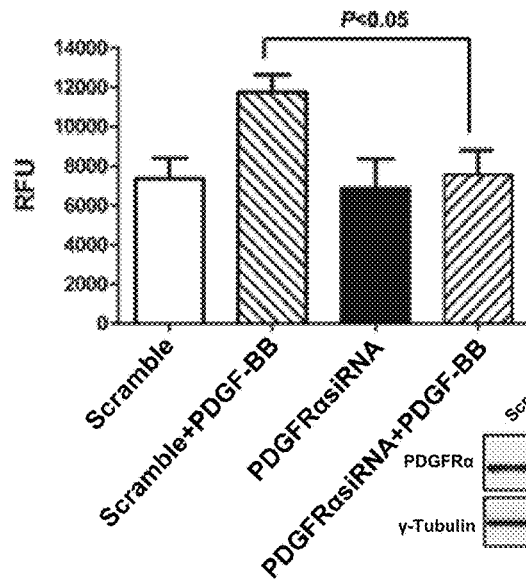
FIG. 7 shows Cytoselect invasion assays with or without PDGFR-α siRNA for TPC-1 cell line (A) with corresponding cell viability assessment (B), invasion assays for 8305C cell line with PDGFR-α siRNA shown in (C) with corresponding cell viability experiment (D)
Figure 7B:
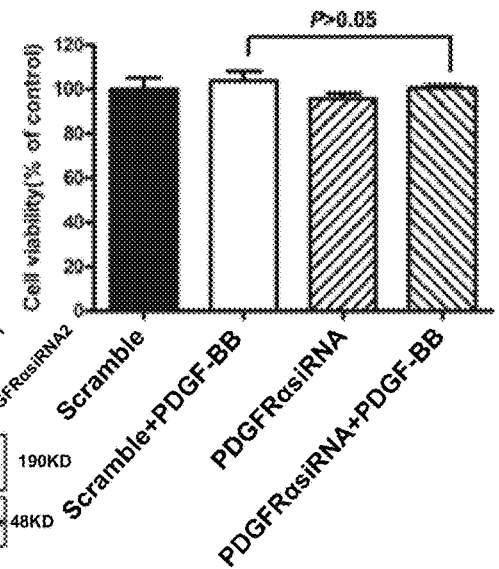
Figure 7C:
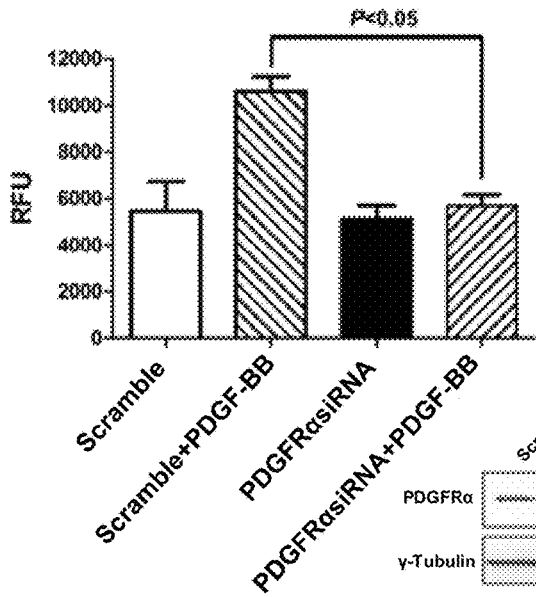
Figure 7D:
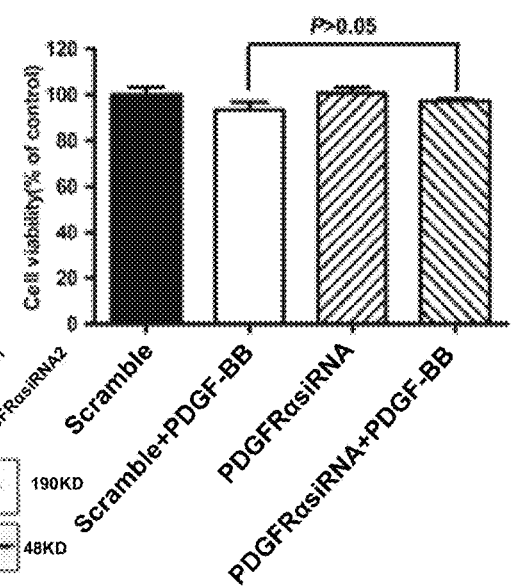

Shown in FIG. 7 are invasion assays in TPC-1 transfected with PDGFR-α siRNA (FIG. 7A) with corresponding cell viability assessments (FIG. 7B). Two different PDGFR-α siRNA constructs were nearly equally effective at decreasing PDGFR-α protein expression in TPC-1 cells as shown in the inset Western blots (FIG. 7A). For the invasion assay in TPC-1 cells using PDGFR-α siRNA1, increases in invasive potential triggered by PDGF-BB stimulation were virtually completely disrupted (FIG. 7A). PDGFR-α siRNA alone did not significantly change invasive potential relative to the controls with scramble RNA. Cell viability was not affected in any of the experiments (FIG. 7B). Qualitatively and quantitatively similar results were seen with siRNA blockade of PDGFR-α in 8305C cells (FIG. 7C). PDGFR-α siRNA could block PDGF-BB mediated increases in invasive potential but no effect was seen in the absence of PDGF-BB. With or without PDGF-BB stimulation, scramble or siRNA constructs had no effect on cell viability (FIG. 7D). PDGFR-α siRNA1 construct was more effective at reducing PDGFR-α protein levels and was used for these experiments in 8305C cells (inset FIG. 7C).

PDGFR-α Activation and Increased Invasion Potential is Mediated by Both the MAPK/ERK and PI3K/Akt Pathways Using Western blots we demonstrate a link between PDGFR activation and up-regulation of both the MAPK/ERK and PI3K/Akt pathways in TPC-1 and 8305C cell lines. We also examine the impact of sunitinib treatment on signal transduction in these cell lines.

Figure 8:
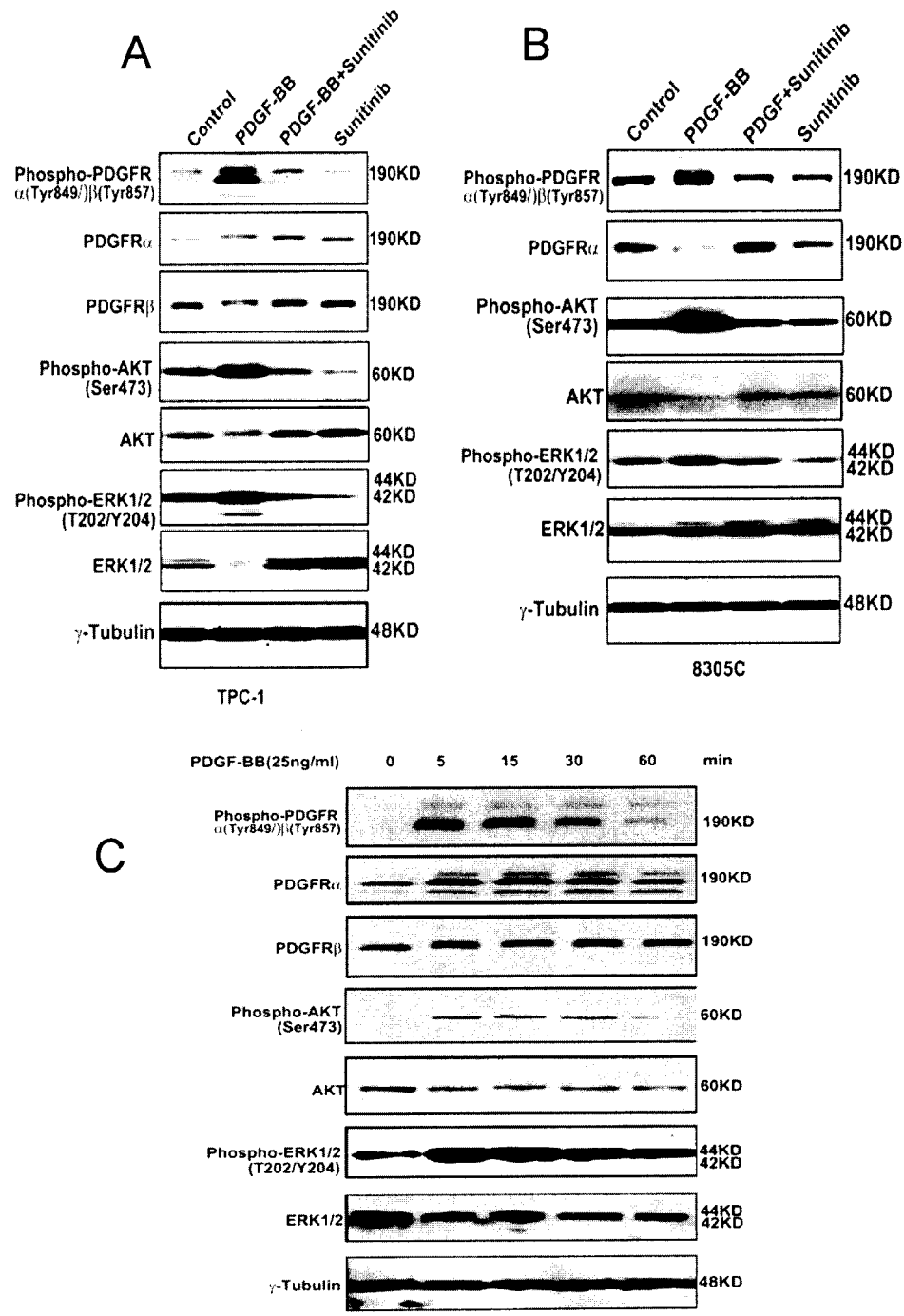
FIGS. 8A-8C show the corresponding Western blots of the TPC-1 (FIG. 8A) and 8305C (FIG. 8B) cell lines for the invasion assay as shown in FIG. 6, and time-dependent changes in activation of PDGFR-α and downstream signaling pathways are shown for TPC-1 in (FIG. 8C)

The corresponding Western blots of the TPC-1 (A) and 8305C (B) cell lines for the invasion assay as shown in FIG. 6, is presented in FIG. 8. Both TPC-1 and 8305C specimens show activation of PDGFR-α (phospho-PDGFR) with corresponding up-regulation of both the PI3K/Akt (phospho-Akt) and MAPK/ERK (phospho-ERK) pathways. Sunitinib completely disrupts PDGFR activation and corresponding up-regulation of downstream MAPK/ERK and PI3K/Akt pathways. The time-dependent changes in activation of PDGFR-α and downstream signaling pathways are shown for TPC-1 in (C). It is clear that the activation of the MAPK/ERK and PI3K/Akt pathways is essentially simultaneous.

Shown in FIG. 8 are the Western blots for (A) TPC-1 and (B) 8305C cell lines examining activation of PDGFR as well as the MAPK/ERK and PI3K/Akt signal transduction pathways. For both cell lines PDGF-BB stimulation leads to strong up-regulation phospho-PDGFR-α/β, phospho-Akt, and phospho-ERK. The degree of up-regulation for the MAPK/ERK pathway was higher in TPC-1 cells than in 8305C which exhibits a small increase in phospho-ERK (FIG. 8). This is likely due to the fact that the MAPK/ERK pathway in 8305C is constitutively activated with its known BRAF mutation (Table 1). It may indicate that activation of PI3K/Akt by BRAF, if operative, does not alter the responsiveness of this pathway to PDGFR signaling. The addition of sunitinib, which we saw previously abated changes in invasive potential in TPC-1 and 8305C cell lines, completely blocks activation of PDGFR-α/β with corresponding significant decreased activity in both the PI3K/Akt and MAPK/ERK pathways (FIG. 8). To confirm that activation of the MAPK/ERK and PI3K/Akt pathways occurred on a similar timescale, we stimulated TPC-1 cells with PDGF-BB and followed expression of phospho-Akt and phospho-ERK over time (FIG. 8C). We demonstrate that PDGF-BB stimulation leads to virtually simultaneous increases in phospho-PDGFR-α/β, phospho-Akt and phospho-ERK within 5 minutes. Both pathways are maximally activated within 15 minutes and levels slowly return to baseline near 60 minutes.

TABLE 1

Experimental papillary thyroid cancer cell lines

| Cell Lines | Histology | RET/PTC | BRAF | PAX8 | TTF1 |
| --- | --- | --- | --- | --- | --- |
| TPC-1 | PTC | + | wt | High | Low |
| BCPAP | PTC | − | V600E | High | High |
| KTC-1 | PTC | − | wt | High | High |
| 8305C | PTC/ATC | − | V600E | Low | High |

We also examined if both the MAPK/EKR and PI3K/Akt pathways are important in mediating changes in invasion potential triggered by PDGFR activation. We used pharmacologic blockade of either the PI3K/Akt or MAPK/ERK pathways in TPC-1 cells and assessed invasion potential as shown in FIG. 9.

Figure 9:
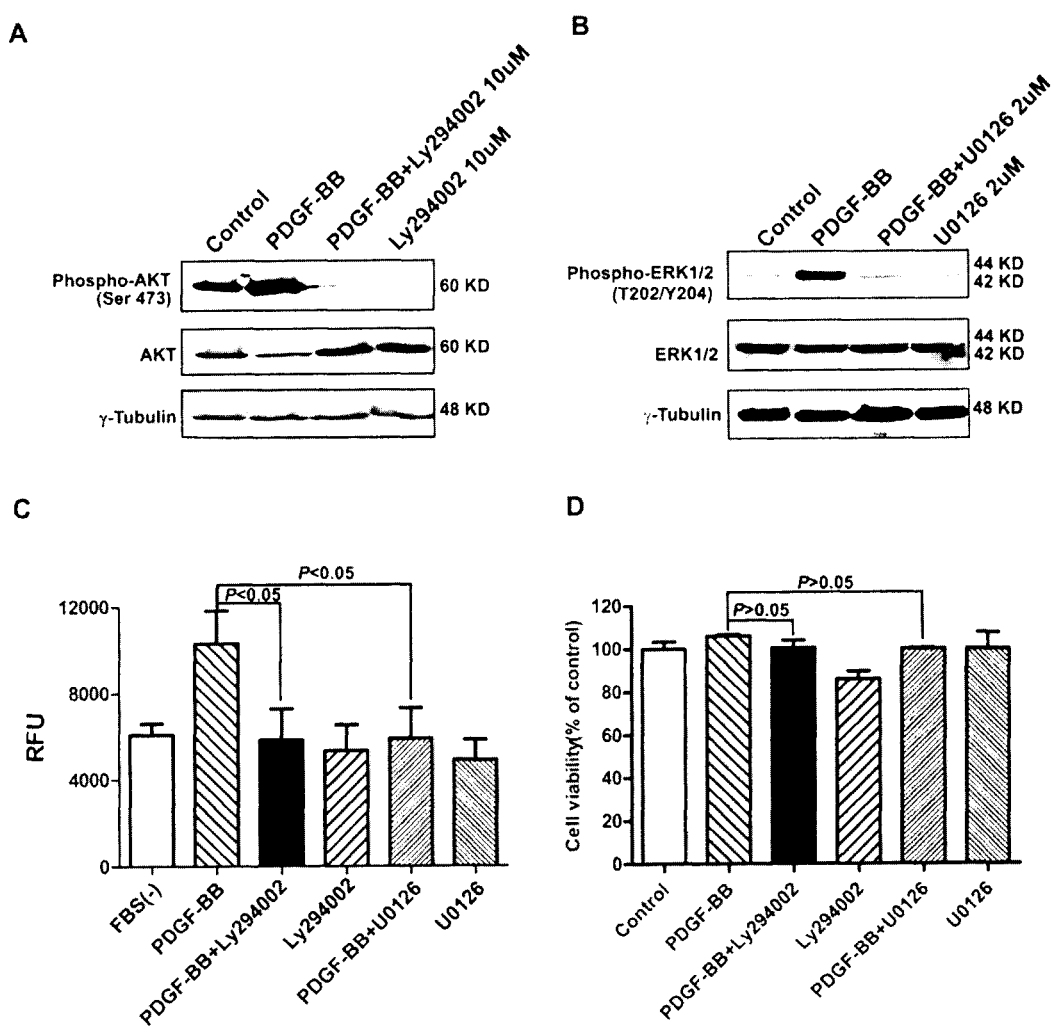
FIG. 9 shows disrupted invasive potential of TPC-1 cells with small molecule inhibition of (A) PI3K/Akt (Ly294002) or (B) MAPK/ERK (U0126) pathways, and bar graphs in (C) and (D)

Disrupted invasive potential of TPC-1 cells with small molecule inhibition of (A) PI3K/Akt (Ly294002) or (B) MAPK/ERK (U0126) pathways with Western blots confirming decreased protein expression is shown in FIG. 9. The invasive assay (C) confirms that blockade of either pathway is sufficient to abrogate increases in invasive potential mediated by PDGF-BB stimulation. Cell viability is not significantly altered by the small molecule inhibitors and does not confound our results (D). RFU=relative fluorescence units.

Western blots of PI3K/Akt blockade (Ly294002) and MAPK/ERK blockade (U0126) in PDGF-BB stimulated TPC-1 cells are shown in FIG. 9. It is clear that blockade of either pathway prevents PDGF-BB mediated increases in invasive potential of the TPC-1 cell line (FIG. 9C). For both pathways, the blockade was nearly complete relative to controls and the viability of the cell lines was not significantly altered. Based on this data, and the Western blots outlined above (FIG. 8), it appears that both the MAPK/ERK and PI3K/Akt pathways play an important role in mediating the effects of PDGFR activation and increased invasive potential.

Discussion

As shown herein, PDGFR-α is strongly associated with lymph node metastases in papillary thyroid cancer. Also, PDGFR-β does not appear to be linked to metastatic disease despite the fact it is clearly expressed in the majority of cancer specimens we surveyed. Neither the α- or β-subunits is expressed at significant levels in normal thyroid tissue. The association of PDGFR-α with a more aggressive, metastatic phenotype in PTC patient specimens was mirrored in studies of invasive potential in PTC experimental cell lines. We demonstrate that PDGFR-mediated changes in invasive potential are directly and strongly related to the presence of PDGFR-α in the different cell lines (FIG. 6). Cell lines with only PDGFR-β did not demonstrate increased invasive potential with PDGFR activation, nor did cell lines with both PDGFR-α and -β that had selective siRNA knockdown PDGFR-α (FIG. 7). While not wishing to be bound by theory, it is believed the α-subunit is important in conveying increased invasive potential and the presence, or absence, of PDGFR-β does not appear modify invasive potential in response to PDGF-BB stimulation. The differential expression of PDGFR and its association with disease progression has important diagnostic considerations and implications for therapy in the choice and design of tyrosine kinase inhibitors to treat metastatic thyroid cancer.

Treatment of metastatic PTC, that in many cases may be resistant to radioactive iodine, is problematic with significant morbidity incurred by patients through repeated surgical resections or high-dose radioactive iodine treatments. Although comprising a relatively small proportion of thyroid cancer patients, these individuals suffer disproportionately and radioactive iodine resistance in thyroid cancer has prompted trials using tyrosine kinase inhibitors to address these difficult cases as reviewed by Gild et al.[39] The drugs used thus far include axitinib, motesanib, sorafenib, and sunitinib. The rationale for selecting these drugs in treating thyroid cancer has essentially been empirical, relying on observations in breast and colon cancer.[40-42] Most of these drugs are multikinase inhibitors that target the different PDGFR and VEGFR to varying degrees and in some cases it is not clear which receptor subgroup is most effectively targeted. Objective responses to TKI therapy in thyroid cancer vary anywhere between zero and 55% but because of the small number of patients treated in these trials, the varying treatment regimes and different outcome measures, it is difficult to draw conclusions.[39,40] Sorafenib and sunitinib appear to have favourable outcomes and acceptable side-effect profiles that permit ongoing use and further phase III trials.[38,43].

As shown herein, PDGFR-α/β signaling is mediated by both the MAPK/ERK and PI3K/Akt pathways in PTC. The cell line experiments herein demonstrate that increased invasive potential mediated by PDGF signaling requires the activity of both pathways. The time course for activation of both pathways was very similar with PDGF-BB stimulation in TPC-1 cells and disruption of either pathway, using small molecule inhibitors, was sufficient to completely abrogate any change in invasive potential with PDGFR activation (FIG. 9). We also show that sunitinib, through blockade of PDGFR signaling, can down-regulate signaling through both pathways effectively.

In summary, PDGFR-α is associated with lymph node metastases in papillary thyroid cancer. The selective and strong expression of the a-subunit, but not PDGFR-β, in primary tumors with lymphatic metastases permits an immunohistochemical test to aid in identifying patients with occult metastases. PDGFR-α also appears to confer increased invasive potential in papillary thyroid cancer cell lines with PDGF-BB stimulation. Downstream signaling is mediated through both the MAPK/ERK and PI3K/Akt pathways and disruption of either pathway can mitigate the effects of PDGFR-activation on cell invasion potential.

Example II

Patients and Methods

Patient Specimens

Ethics approval was obtained through the University of Alberta Heath Research Ethics Board ID Pro00018758. Specimens prepared for primary cell culture or tissue banking were placed in culture media or OCT (Optimal Cutting Temperature compound), respectively, within 10 minutes of devascularisation. For the tissue array with paraffin specimens, a total of 124 patients were selected with papillary thyroid carcinoma, 66 without and 58 with lymphatic metastases. In all cases patients had a total thyroidectomy with a level VI lymph node dissection such that histopathology could be used to document the true node negative cases. Two pathologists separately assessed the specimens to document primary tissue diagnosis as well as the presence of lymphatic metastases in nodes sectioned.

Reagents and Antibodies

The Mek inhibitor U0126 and PI3K inhibitor Ly294002 were from Cell Signaling (Danvers, USA) and used at 10 and 50 uM respectively. Sunitinib malate was purchased from TORCIS Bioscience (Ellisville, USA) and used at 0.25 umol/L. STAT3 inhibitor was purchased from Santa Cruz Biotechnology, (Santa Cruz, USA). Tetramethylrhodamine ethyl ester (TMRE) was purchased from Molecular Probes.

The following antibodies were used for immunoblotting and for staining the paraffin tissue arrays: phospho-Erk1/2 (Thr 202/Tyr204) (E10: #9106), Akt (#9272), phospho-Akt (Ser473) (587F11: #4051), PDGFR-α (D1E1E:#3174), phospho-PDGFR-α/β (Tyr849)/(Tyr857) (C43E9: #3170), were all from Cell Signaling Technology (Danvers, USA). The PDGFR-β antibody and total Erk1 antibody (K-23: sc94) were from Santa Cruz Biotechnology, (Santa Cruz, USA).

Cell Culture

TPC-1 and BCPAP experimental cell lines were generously provided by Dr. S. Ezzat, University of Toronto, Canada. 8305C was purchased from DSMZ (Braunschweig, Germany). RET/PTC (TPC-1) and BRAF (BCPAP, 8305C) mutation status and thyroid cell origin was confirmed using Pax-8 and TTF-1 staining.[37] Primary cell culture and experimental cell lines were maintained in RPMI 1640 media supplemented with 10% FBS.

Western Blot Analyses

Cells were lysed in RIPA buffer [150 mM NaCl, 100 mM Tris (pH 8.0), 1% Triton X-100, 1% deoxycholic acid, 0.1% SDS, 5 mM EDTA, and 10 mM NaF] supplemented with 1 mM sodium vanadate, 2 mM leupeptin, 2 mM aprotinin, 1 mM phenylmethylsulfonyl fluoride (PMSF), 1 mM DTT, 2 mM pepstatin, and 1:100 protease inhibitor cocktail set III on ice. After centrifugation at 4° C. at 18,000 rpf for 15 min, the supernatant was harvested as the total cellular protein extracts, aliquoted and stored at −80° C. The protein concentration was determined using Bio-Rad protein assay reagent (Richmond, USA). Aliquots of protein extract samples were separated by SDS-polyacrylamide gel electrophoresis (SDS-PAGE) and transferred to nitrocellulose membrane. Membranes were blocked with 5% nonfat milk in TBS containing 0.05% Tween-20 for 60 min, followed by incubation with primary antibodies 4° C. overnight. Protein bands were detected by incubation with horseradish peroxidase-conjugated antibodies (Pierce Biotechnology, Rockford, Ill., USA) and visualized with SuperSignal West Pico chemiluminescence substrate (Thermo Scientific, Rockford, Ill., USA).

Short Hairpin (shRNA) Stable Transductions

To selectively and stably silence the expression of the PDGFR-alpha and -beta receptors in the TPC-1, BCPAP and 8305C cell lines we used the HuSH-29 shRNA Vector system (HuSH-29 shRNA Retroviral Vector Systems; OriGene Technologies, Inc.). Briefly, to silence the expression of the PDGFR-alpha receptor PTC cells were transduced with the pRS shRNA retrovirus system (Puro+) followed by selection in puromycin (2.5 ug/mL). Resistant cells were assessed by western blot to select the sequences that produced the highest levels of protein expression knock-down. The sequences used for these studies were GATGCCTGGCTAAGAATCTCCTTGGAGCT (SEQ ID NO: 1) for the TPC-1 cell line and

```
AGTTCCACCTTCATCAAGAGAGAGGACGA      (SEQ ID NO: 2)
``` for the 8305C cell line. To selectively knock down the PDGFR-beta receptor were transduced with the pGFP-BR-S shRNA retrovirus system (BSD+) followed by selection in blasticidin (500 ug/mL). Resistant cells were again assessed by western blot to select the sequences that produced the highest levels of protein expression knock-down. The sequences selected for these studies were TGCCTCCGACGAGATCTATGAGATCATGC (SEQ ID NO: 3) for the TPC-1 cell line and

```
ACCTTCTCCAGCGTGCTCACACTGACCAA      (SEQ ID NO: 4)
``` for the BCPAP cell line.

Transient transfections of TCP-1, 8305C cells (3×10⁶ cells) were performed using the Electro square electroporator BTX ECM 800 (225V, 8.5 ms, 3 pulses). 1 nmol/L of siRNA or scrambled control was used in 3 million of TPC-1 and 8305C cells. The efficiency of target gene inhibition was assessed after 48 hours transfection by using Western blotting. TPC-1, BCPAP and 8305C were transfected with either PDGFR-α siRNA or scramble siRNA, and starved overnight prior test. siRNA for PDGFR-α and scrambled siRNA were purchased from Siegen (Foster, Calif., USA). Transfected PTC cell lines were plated at a density of 10,000 or 20,000/ml and cultured for 5 days. Invasive cells passed through basement membrane layer and dissociated from the membrane using detachment buffer and quantified using CyQuant GR fluorescent dye.

Wound Healing, Clonogenic and Transwell Invasion Assays

Cytoselect™ 24-well cell invasion basement membrane assay kit (Cell Biolabs, San Diego, USA) was used to measure the invasive properties of the cells. Briefly, the stable TPC-1 cell lines were seeded at a density of 3×10⁵ cells/well and cultured for 48 hours, as previously described[37]. Invasive cells passed through the basement membrane layer, dissociated using detachment buffer and then quantified by means of CyQuant GR fluorescent dye.

Adherent colony formation assays were performed as described (REF#I). Fifty or 100 cells per well were plated in six-well plates, fed 5% FBS supplemented growth medium and allowed to form colonies for 20 days. Colonies were stained with 0.5% crystal violet solution in 25% methanol and counted. The methylcellulose was used assess anchorage-independent growth capabilities of the cell lines.

For the wound healing assay, cells were plated in 6 well plates at 80-90% confluence. A wound was created by manually scratching the cell monolayer with a p1000 pipet tip. Cellular debris was washed with PBS and the cells were fed with complete growth medium or serum-free medium. Images and measurements were acquired at times 0, 20 and 44 hours after wound creation.

Proliferation and Apoptosis Assays

To document the effect of PDGFR silencing on proliferation, cultures were incubated in regular or serum-free-medium and enumerated daily for 5 days with an electronic cell counter (Coulter Model Zf). The MTS assay (Promega, Madison, USA) was also performed in 8-16 replicates after 48 and 72 hours of growth.

Statistical Analysis

Data were expressed as the mean±S.E. from a minimum of three independent experiments. Statistical analyses were performed with a completely random design one-way ANOVA. The correlations between protein expression and metastatic status were assessed using Fisher's exact test for tables and Spearman rank correlation for continuous variables. Statistical tests are two-tailed with a P value <0.05 considered to be statistically significant. The SAS computer program SAS (r) 9.2 (TS1M0) was used to perform the analysis.

Results II

Figure 10:
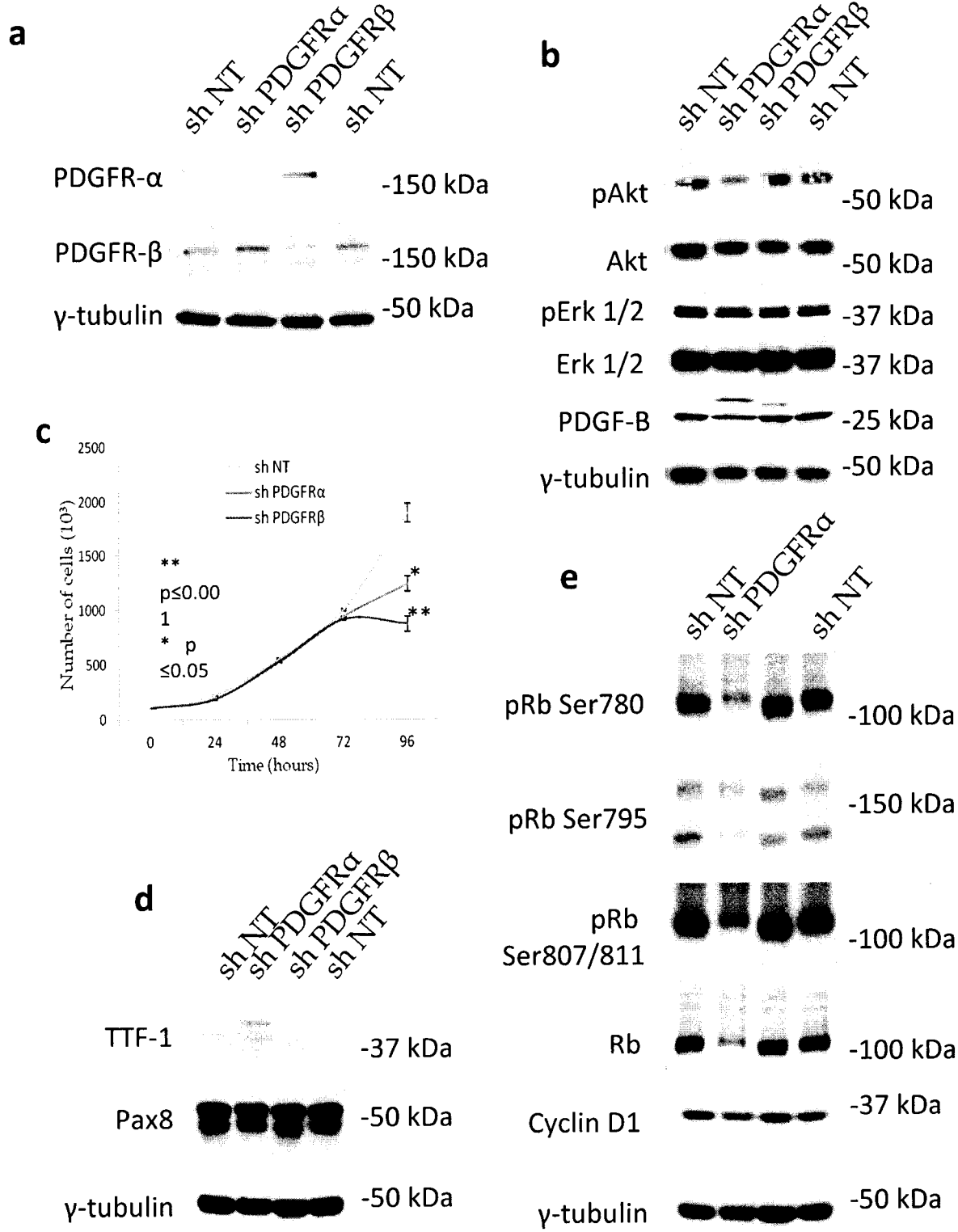
FIGS. 10A-10F depict the selective knock down of the PDGFR-alpha and -beta subunits in the TPC-1 cell lines; protein expression levels were assessed by immunoreactivity to the PDGFR-alpha or PDGFR-beta antibodies (FIG. 10A); activity of signaling molecules in the STAT5, PI3K and MAPK pathways as well as expression of PDGF-BB was documented by immunoblotting with phosphospecific antibodies (FIG. 10B); growth rate was assessed in serum free medium and cells enumerated at 24, 48, 72 and 96 hours (FIG. 10C); protein expression of thyroid differentiation markers was assessed by immunoreactivity to the TTF-1 and Pax8 antibodies (FIG. 10D); tumour suppressor protein Rb and cell cycle marker protein D1 were documented by immunoblotting (FIG. 10E); where cells were synchronized at the G1/S border by a double thymidine block then released and followed with propidium iodide staining at the indicated time points and flow cytometry analysis (FIG. 10F)

The Experiments of FIG. 10 depict selective knock down of the PDGFR-alpha and -beta subunits in the TPC-1 cell lines. In Panel (a) protein expression levels were assessed by immunoreactivity to the PDGFR-alpha or PDGFR-beta antibodies. In Panel (b) activity of signaling molecules in the STAT3, PI3K and MAPK pathways as well as expression of PDGF-BB was documented by immunoblotting with phosphospecific antibodies. PDGFR-alpha signaling is strongly linked to PI3IC/Akt pathway. In Panel (c) growth rate was assessed in serum free medium and cells enumerated at 24, 48, 72 and 96 hours. In Panel (d) protein expression of thyroid differentiation markers was assessed by immunoreactivity to the TTF-1 and Pax8 antibodies. It is noted that PDGFR-alpha expression is linked to dedifferentiated cells lacking expression of TTF-1 but when PDGFR-alpha is knocked-down expression of the differentiation marker is restored. In Panel (e) tumour suppressor protein Rb and cell cycle marker protein D1 were documented by immunoblotting. While total levels of Rb varied the relative phosphorylated Rb to total Rb ratio did not change significantly indicating that cell cycle was not altered by PDGFR-alpha or -beta expression. This was confirmed in panel (f) where cells were synchronized at the G1/S border by a double thymidine block then released and followed with propidium iodide staining at the indicated time points and flow cytometry analysis. There was no difference between the different cell lines expressing PDGFR-alpha or -beta in cell cycle analysis.

Increased cell size and colony formation are indicative features of cancer cells taking on a migratory and more aggressive phenotype.

Figure 11:
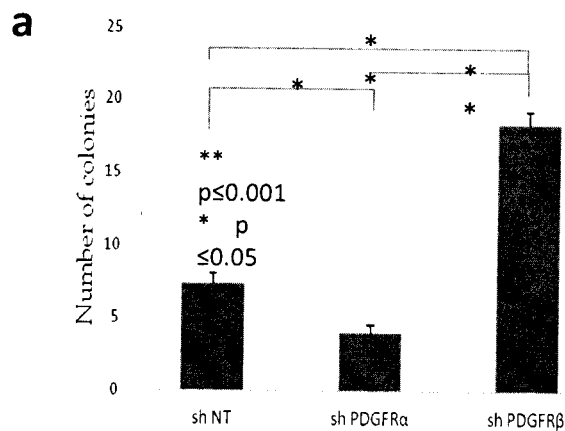
FIGS. 11A-11F show that knockdown of the PDGFR-beta subunit increases colony formation in the TPC-1 cell line while selective PDGF-alpha expression increases cell size in the TPC-1 and BCPAP cell lines; TPC-1 colony formation assay demonstrates that PDGFR-alpha, when signaling without PDGFR-beta, induces more colonies to form (FIG. 11A); TPC-1 cell size also increased when PDGFR-alpha is expressed in the absence of PDGFR-beta (FIG. 11B); TPC-1-representative photographs of cells with the various knock-downs of PDGFR-alpha or beta (FIG. 11C); in BCPAP cells, a decrease is evident in expression of TTF-1 differentiation marker with expression of PDGFR-alpha as assessed by immunoreactivity to the PDGFR-alpha, TTF-1, Pax8 and Akt antibodies (FIG. 11D); as with TPC-1 cells, the cell size increases with PDGFR-alpha expression in BCPAP cells (FIG. 11E); representative photographs of BCPAP cells (FIG. 11F)
Figure 11:
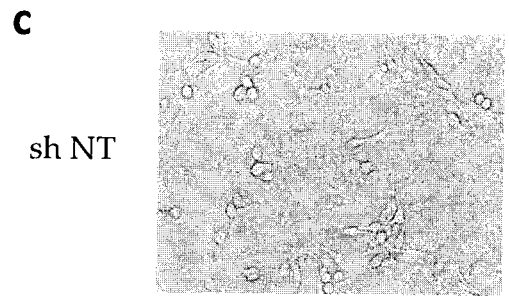
Figure 11:
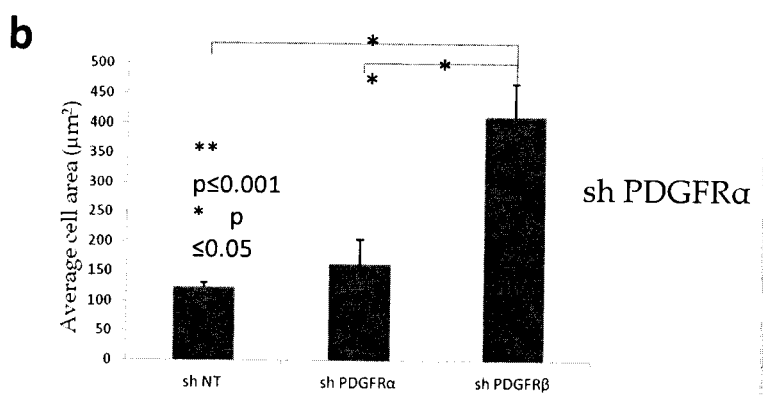
Figure 11:
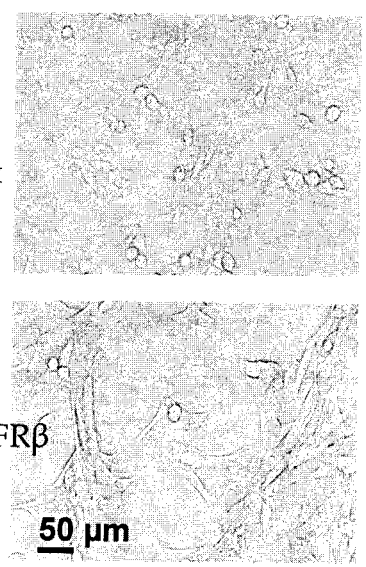
Figure 11:
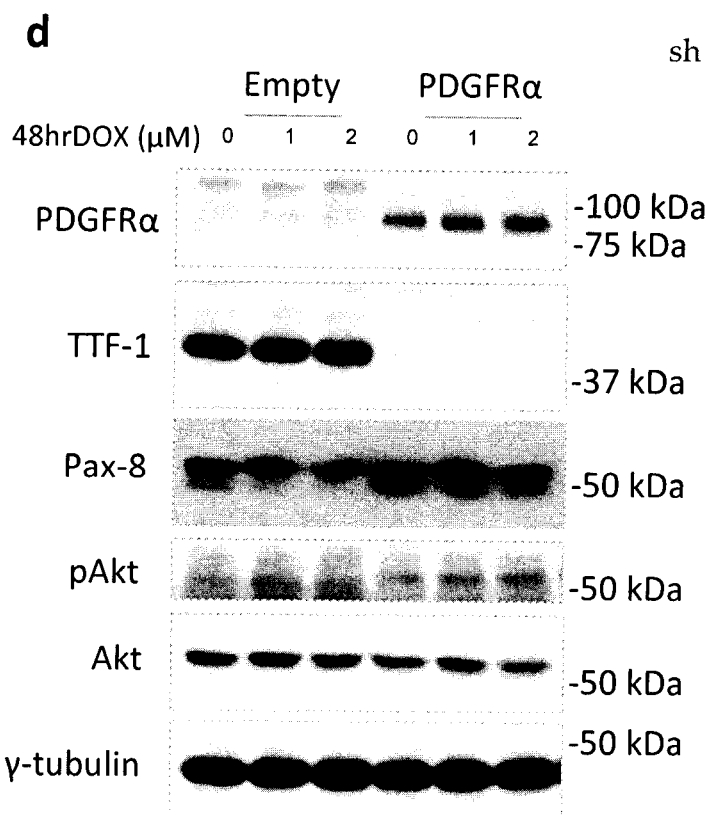
Figure 11:
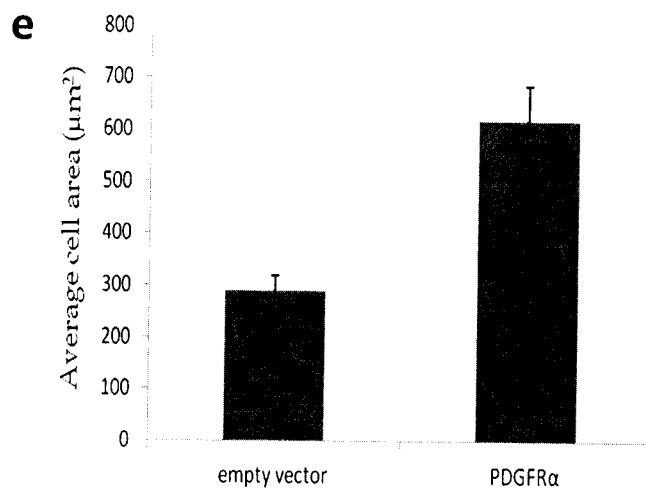
Figure 11:
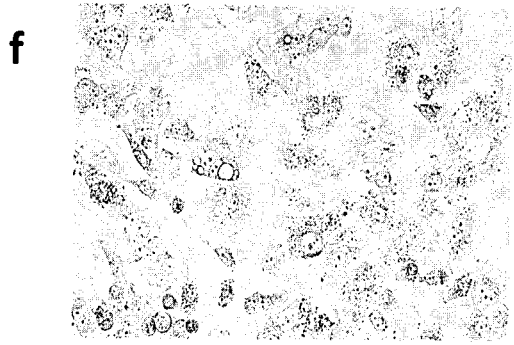
Figure 11:
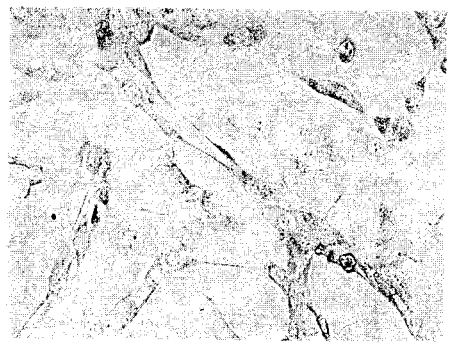
Figure 12:
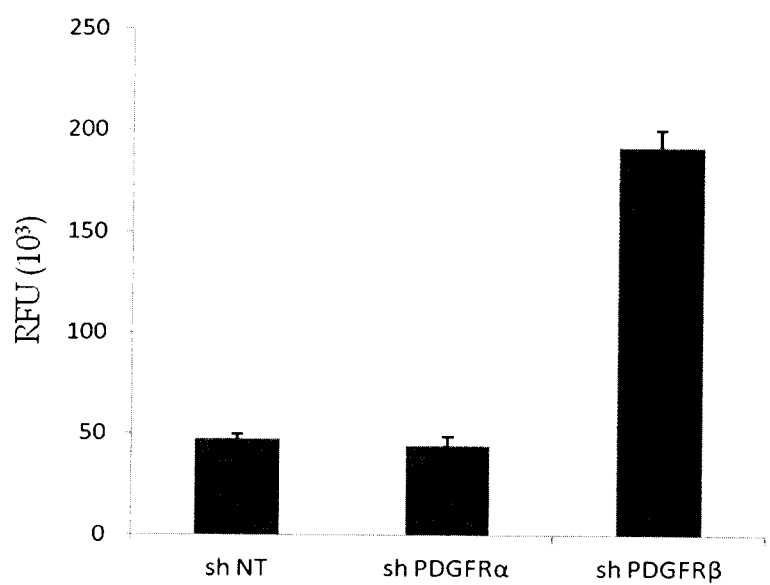
FIG. 12 shows that PDGFR-alpha subunit drives cell migration in TPC-1, BCPAP and 8305C cell lines.

The experiments of FIG. 11 depict that expression of PDGFR-alpha and knockdown of the PDGFR-beta subunit increases colony formation and cell size. In Panel (a) TPC-1 colony formation assay demonstrates that PDGFR-alpha, when signaling without PDGFR-beta, induces more colonies to form. In Panel (b) TPC-1 cell size also increased when PDGFR-alpha is expressed in the absence of PDGFR-beta. In Panel (c) TPC-1-representative photographs of cells with the various knock-downs of PDGFR-alpha or -beta. In Panel (d) BCPAP—a decrease is evident in expression of TTF-1 differentiation marker with expression of PDGFR-alpha as assessed by immunoreactivity to the PDGFR-alpha, TTF-1, Pax8 and Akt antibodies. In Panel (e) as with TPC-1, the cell size increases with PDGFR-alpha expression in BCPAP cells. In Panel (f) BCPAP—representative photographs. Scale bar, 50 μm. The experiments of FIG. 12 depict that cancer cell lines stably expressing shRNA show similar invasive potential as siRNA treatment, namely that PDGFR-alpha subunit alone drives invasive potential in TPC-1 cell lines. Invasive potential of cells where PDGFR-beta expression is knocked down, but not PDGFR-alpha is increased as shown using the basement membrane cell invasion assay kit. After 48 hours incubation, invasive cells were dissociated, lysed, and quantified by CyQuant GR Dye.

Figure 13:
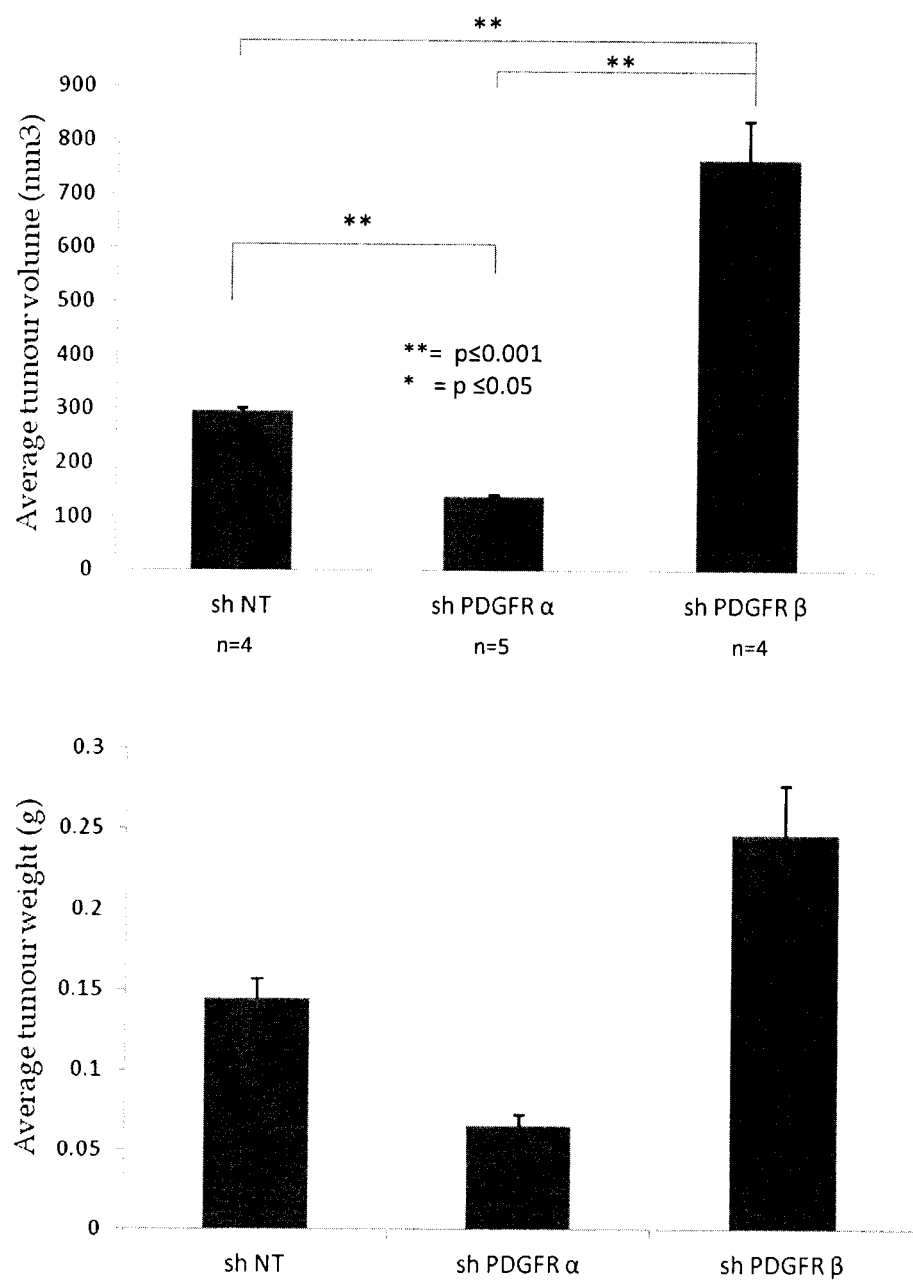
FIG. 13 shows knock down of PDGFR-alpha or -beta subunits results in opposing effects in tumour formation on a mice xenograft model.

The experiments of FIG. 13 depict knock down of PDGFR-alpha or -beta subunit results in opposing effects in tumour formation on a mice xenograft model. Mice (4 or 5 animals per group as indicated) were inoculated with sh NT (Scrambled), sh PDGFR-alpha (alpha knock down) or sh PDGFR-beta (beta knock down) TPC-1-derived cell lines in Matrigel. The average tumour volume (top panel) and tumour weight (bottom panel) was much higher for mice given cell lines expressing only PDGFR-alpha and statistical significance between groups were calculated 20 days after inoculation.

Figure 14:
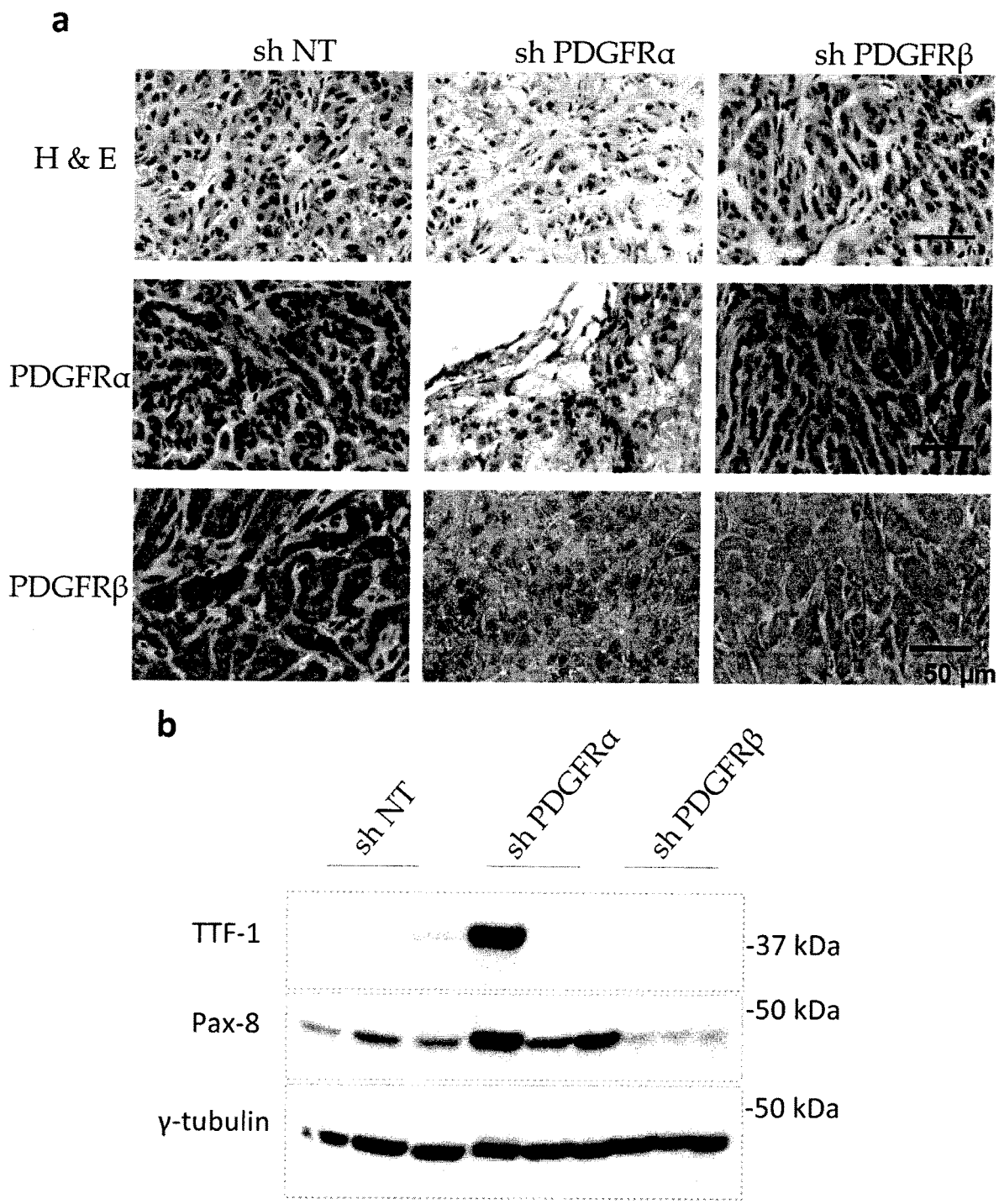
FIG. 14 shows immunohistochemical and immunoblot results from mouse xenographts.

In the experiments of FIG. 14, Panel (a) shows immunohistochemical pattern of PDGFR subunit expression in the mouse xenografts. The PDGFR-alpha only tumors are more invasive and demonstrate a more diffuse growth pattern than the more differentiated PDGFR-beta expressing tumors. Scale bar, 50 μm. In Panel (b) immunoblots show expression of thyroid markers in the mice xenograft implantations demonstrating that tumors in mice with PDGFR-alpha are dedifferentiated thus lacking TTF-1 expression. This correlates with the in vitro results.

In the experiments of FIG. 15, there is present the data from analysis of an SABiosciences PI3K/Akt mRNA array demonstrating that PDGFR-alpha mRNA levels in metastatic specimens from human patients are more than 5 times that in primary tumors. In these experiments RNA was isolated from either primary tumors ("1 tumor") or metastatic tumors ("Mets"). The RNA was converted to cDNA, and analyzed using an SABiosciences PCR Array (PI3K-AKT Signaling PCR Array) which contains a preset mix of primers for genes in the signaling pathway (including PDGFα), together with the software to analyze the result.

Discussion II

From the foregoing experiments it is evident that expression of PDGFR alpha leads to two main changes in cell lines; the first is that the cells become more invasive as based on invasion assays and secondly, in multiple cell lines, PDGFR alpha leads to dedifferentiation, both of which are associated with more aggressive metastatic tumors.

This was further demonstrated in the experiments in which tumors in mice from transplanted PDGFR alpha expressing thyroid cancer cells were larger by weight and volume than cell lines that only expressed PDGFR beta. The combination of PDGFR alpha and beta demonstrated an intermediate phenotype compared to the slow growing, less aggressive PDGFR beta only expressing cells and the most aggressive PDGFR alpha only cells.

PDGFR subunits alpha and beta thus modulate the others activity in cells such that the cell phenotype can be determined depending on whether alpha, beta or both subunits is expressed. This is consistent with the clinical specimens described herein, where most of the thyroid cancers expressed PDGFR beta, regardless of their metastatic status, but only the more aggressive metastatic specimens expressed PDGFR alpha. Tumors that did not express PDGFR alpha did not typically demonstrate lymphatic metastases. It was also shown that in human specimens that PDGFR-alpha gene expression levels are more than five times higher in metastases than in primary tumours (P=0.013) (FIG. 15).

REFERENCES

1. Dean D S, Gharib H. Epidemiology of thyroid nodules. Best Pract Res Clin Endocrinol Metab. 2008; 22:901-11.
2. Gharib H, Goellner J R. Fine-needle aspiration biopsy of the thyroid: an appraisal. Ann Intern Med. 1993; 118:282-9.
3. Cooper D S, Doherty G M, Haugen B R, Kloos R T, Lee S L Lee S L, Mandel S J, Manaferri E L, McIver B, Pacini F, Schlumberger M, Sherman S I, Steward D L, Tuttle R M. Revised American Thyroid Association management guidelines for patients with thyroid nodules and differentiated thyroid cancer. American Thyroid Association (ATA) Guidelines Taskforce on Thyroid Nodules and Differentiated Thyroid Cancer, Thyroid. 2009; 19:1167-1214.
4. Crowe A, Linder A, Hameed O, et al. The impact of implementation of the Bethesda system for reporting thyroid cytopathology on the quality of reporting, "risk" of malignancy, surgical rate, and rate of frozen sections requested for thyroid lesions. Cancer Cytopathol. 2011 [epub ahead of print]
5. Yip L, Kebebew E, Milas M, Carty S E, Fahey T J 3rd, Parangi S, Zeiger M A, Nikiforov Y E. Summary statement: utility of molecular marker testing in thyroid cancer. Surgery. 2010; 148:1313-5.
6. Udelsman R. Treatment of persistent or recurrent papillary carcinoma of the thyroid—the good, the bad, and the unknown. J Clin Endocrinol Metab. 2010; 95:2061-2063
7. Tee Y Y, Lowe A J, Brand C A, Judson R T. Fine-needle aspiration may miss a third of all malignancy in palpable thyroid nodules: a comprehensive literature review. Ann Surg. 2007; 246:714-20.
8. Shaha A R, Shah J, Loree T R. Patterns of failure in differentiated carcinoma of the thyroid based on risk groups. Head Neck. 1998; 20:26-30.
9. Machens A, Hinze R, Thomusch O, Dralle H. Pattern of nodal metastasis for primary and reoperative thyroid cancer, World J Surg. 2002; 26:22-28.

10. Ito Y, Miyauchi A. Lateral lymph node dissection guided by preoperative and intraoperative findings in differentiated thyroid carcinoma. World J Surg. 2008; 32:729-39.
11. Rotstein L. The role of lymphadenectomy in the management of papillary carcinoma of the thyroid. J Surg Oncol. 2009; 99:186-188.
12. Sywak M, Cornford L, Roach P, Stalberg P, Sidhu S, Delbridge L. Routine ipsilateral level VI lymphadenectomy reduces postoperative thyroglobulin levels in papillary thyroid cancer. Surgery. 2006; 140:1000-1005
13. Lundgren C I, Hall P, Dickman P W, Zedenius J. Clinically significant prognostic factors for differentiated thyroid carcinoma: a population-based, nested case-control study. Cancer. 2006; 106:524-31.
14. Shibru D, Chung K W, Kebebew E. Recent developments in the clinical application of thyroid cancer biomarkers. Curr Opin Oncol. 2008; 20:13-18.
15. Taccaliti A, Boscaro M. Genetic mutations in thyroid carcinoma. Minerva Endocrinol. 2009; 34:11-28.
16. Marchetti I, Lessi F, Mazzanti C M, Bertacca G, Elisei R, Coscio G D, Pinchera A, Bevilacqua G. A morpho-molecular diagnosis of papillary thyroid carcinoma: BRAF V600E detection as an important tool in preoperative evaluation of fine-needle aspirates. Thyroid. 2009; 19:837-842
17. Zatelli M C, Trasforini G, Leoni S, Frigato G, Buratto M, Tagliati F, Rossi R, Cavazzini L, Roti E, degli Uberti E C. BRAF V600E mutation analysis increases diagnostic accuracy for papillary thyroid carcinoma in fine-needle aspiration biopsies. Eur J Endocrinol. 2009; 161:467-473.
18. DeLellis R A. Pathology and genetics of thyroid carcinoma. J Surg Oncol. 2006; 94:662-669.
19. Nikiforov Y E. Thyroid carcinoma: molecular pathways and therapeutic targets. Mod Pathol. 2008; 21:537-43.
20. Chiu C G, Strugnell S S, Griffith O L, Jones S J, Gown A M, Walker B, Nabi I R, Wiseman S M. Diagnostic utility of galectin-3 in thyroid cancer. Am J Pathol. 2010; 176:2067-2081.
21. Griffith O L, Chiu C G, Gown A M Jones S J, Wiseman S M. Biomarker panel diagnosis of thyroid cancer: a critical review. Expert Rev Anticancer Ther. 2008; 8:1399-1413.
22. Griffith O L, Melck A, Jones S J, Wiseman S M. Meta-analysis and meta-review of thyroid cancer gene expression profiling studies identifies important diagnostic biomarkers. J Clin Oncol. 2006; 124:5043-51.
23. Shibru D, Hwang J, Khanafshar E, Duh Q Y, Clark O H, Kebebew E. Does the 3-gene diagnostic assay accurately distinguish benign from malignant thyroid neoplasms? Cancer. 2008; 113:930-5.
24. Chiu C G, Strugnell S S, Griffith O L, Jones S J, Gown A M, Walker B, Nabi I R, Wiseman S M. Diagnostic utility of galectin-3 in thyroid cancer. Am J Pathol. 2010; 176:2067-81.
25. Nikiforov Y E, Ohori N P, Hodak S P, Carty S E, Lebeau S O, Ferris R L, Yip L, Seethala R R, Tublin M E, Stang M T, Coyne C, Johnson J T, Stewart A F, Nikiforova M N. Impact of Mutational Testing on the Diagnosis and Management of Patients with Cytologically Indeterminate Thyroid Nodules: A Prospective Analysis of 1056 FNA Samples. J Clin Endocrinol Metab. 2011 [epub August 31].
26. Lee S H, Lee J K, Jin S M Lee K C, Sohn J H, Chae S W, Kim D H. Expression of cell-cycle regulators (cyclin D1, cyclin E, p27kip 1, p57kip2) in papillary thyroid carcinoma. Otolaryngol Head Neck Surg. 2010; 142:332-337.
27. Liang H, Zhong Y, Luo Z, Huang Y, Lin H, Luo M, Zhan S, Xie K, Ma Y, Li Q Q. Assessment of biomarkers for clinical diagnosis of papillary thyroid carcinoma with distant metastasis. Int J Biol Markers. 2010; 25:38-45.
28. Zhu X, Sun T, Lu H, Zhou X, Lu Y, Cai X, Zhu X. Diagnostic significance of CK19, RET, galectin-3 and HBME-1 expression for papillary thyroid carcinoma. J Clin Pathol. 2010; 63:786-9. [Epub 2010 Jul. 19].
29. Gu L Q, Li F Y, Zhao L, Liu Y, Chu Q, Zang X X, Liu J M, Ning G, Zhao Y J. Association of XIAP and P2X7 receptor expression with lymph node metastasis in papillary thyroid carcinoma. Endocrine. 2010; 38:276-82.
30. Homsi J, Daud A I. Spectrum of activity and mechanism of action of VEGF/PDGF inhibitors. Cancer Control. 2007; 14:285-94.
31. Provencio M, Garcia-Campelo R, Isla D, de Castro J. Clinical-molecular factors predicting response and survival for tyrosine-kinase inhibitors. Clin Transl Oncol. 2009; 11:428-436.
32. Liu J, Liao S, Huang Y, Samuel R, Shi T, Naxerova K, Huang P, Kamoun W, Jain R K, Fukumura D, Xu L. PDGF-D improves drug delivery and efficacy via vascular normalization, but promotes lymphatic metastasis by activating CXCR4 in breast cancer. Clin Cancer Res. 2011; 17:3638-3648.
33. Lei H, Velez G, Kazlauskas A. Pathological signaling via platelet-derived growth factor receptor {alpha} involves chronic activation of Akt and suppression of p53. Mol Cell Biol. 2011; 31:1788-1799.
34. Cornelià H, Alsinet C, Villanueva A. Molecular pathogenesis of hepatocellular carcinoma. Alcohol Clin Exp Res. 2011; 35:821-825.
35. Yano Y, Uematsu N, Yashiro T. Gene expression profiling identifies platelet-derived growth factor as a diagnostic molecular marker for papillary thyroid carcinoma. Clin Cancer Res 2004; 10:2035-43.
36. Bruland O, Fluge Ø, Akslen L A et al. Inverse correlation between PDGFC expression and lymphocyte infiltration in human papillary thyroid carcinomas. BMC Cancer 2009; 9:425-432.
37. Wang Y, Ji M, Wang W, Miao Z, Hou P, Chen X, Xu F, Zhu G, Sun X, Li Y, Condouris S, Liu D, Yan S, Pan J, Xing M. Association of the T1799A BRAF mutation with tumor extrathyroidal invasion, higher peripheral platelet counts, and over-expression of platelet-derived growth factor-B in papillary thyroid cancer. Endocr Relat Cancer. 2008; 15:183-90.
38. Sherman S I. Targeted therapies for thyroid tumors. Mod Pathol. 2011 April; 24 Suppl 2:S44-52.
39. Gild M L, Bullock M, Robinson B G, Clifton-Bligh R. Multikinase inhibitors: a new option for the treatment of thyroid cancer. Nat Rev Endocrinol. [Epub 2011 Aug. 23].
40. Romagnoli S, Moretti S, Voce P, Puxeddu E. Targeted molecular therapies in thyroid carcinoma. Arq Bras Endocrinol Metabol. 2009; 53:1061-73.
41. Gupta-Abramson V, Troxel A B, Nellore A et al. Phase II trial of sorafenib in advanced thyroid cancer. J Clin Oncol. 2008; 26:4714-9.
42. Kloos R T, Ringel M D, Knopp M V et al. Phase II trial of sorafenib in metastatic thyroid cancer J Clin Oncol. 2009; 27:1675-1684.
43. Can L L, Mankoff D A, Goulart B H, Eaton K D, Capell P T, Kell E M, Bauman J E, Martins R G. Phase II study of daily sunitinib in FDG-PET-positive, iodine-refractory differentiated thyroid cancer and metastatic medullary carcinoma of the thyroid with functional imaging correlation. Clin Cancer Res. 2010; 16:5260-8.

44. Brose M S, Nutting C M, Sherman S I, Shong Y K, Smit J W, Reike G, Chung J, Kalmus J, Kappeler C, Schlumberger M. Rationale and design of decision: a double-blind, randomized, placebo-controlled phase III trial evaluating the efficacy and safety of sorafenib in patients with locally advanced or metastatic radioactive iodine (RAI)-refractory, differentiated thyroid cancer. BMC Cancer. 2011; 11:349-356.
45. Schweppe R, Klopper J, Korch C et al. Deoxyribonucleic Acid Profiling Analysis of 40 Human Thyroid Cancer Cell Lines Reveals Cross-Contamination Resulting in Cell Line Redundancy and Misidentification. J Clin Endocrinol Metab 2008; 93:4331-4341.
46. Wang P, Wu F, Zhang J, McMullen T, Young L C, Ingham R J, et al. Serine phosphorylation of NPM-ALK, which is dependent on the auto-activation of the kinase activation loop, contributes to its oncogenic potential. Carcinogenesis. 2011; 32:146-53.
47. Tambouret R, Geisinger K R, Powers C N, Khurana K K, Silverman J F, Bardales R, Pitman M B. The clinical application and cost analysis of fine-needle aspiration biopsy in the diagnosis of mass lesions in sarcoidosis. Chest. 2000; 117:1004-1011.
48. Morgenthau A S, Iannuzzi M C. Recent advances in sarcoidosis.Chest. 2011 January; 139(1):174-82.
49. Russell M R, Liu Q, Lei H, Kazlauskas A, Fatatis A. The alpha-receptor for platelet-derived growth factor confers bone-metastatic potential to prostate cancer cells by ligand- and dimerization-independent mechanisms. Cancer Res. 2010; 70:4195-203.
50. Eckert M A, Lwin T M, Chang A T, Kim J, Danis E, Ohno-Machado L, Yang J. Twist1-induced invadopodia formation promotes tumor metastasis. Cancer Cell. 2011; 19:372-86.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

The embodiments of the invention in which an exclusive property or privilege is claimed are defined as follows:

1. A method comprising:
   a) obtaining a sample from a subject with thyroid cancer;
   b) processing said sample;
   c) performing an analyte binding assay comprising contacting the processed sample with a reagent to form a complex between the reagent and a biomarker present in the sample;
   d) generating a result using instrumentation configured to detect said complex, said result indicative of the amount or concentration of said complex formed to determine the amount or concentration of said biomarker in the sample; and
   e) administering a treatment for metastatic papillary thyroid cancer to said subject when the amount of the biomarker in the sample is greater than that in a control sample,
   wherein said biomarker is PDGFR-α (platelet-derived growth factor receptor α) or a PDGFR-α transcript,
   wherein said treatment comprises administering an inhibitor of PDGFR-α to said subject; and
   surgical resection, radio therapy, or combinations thereof,
   wherein said reagent comprises an antibody that binds to the PDGFR-α or a nucleic acid molecule that binds to the PDGFR-α transcript, and
   wherein said inhibitor of PDGFR-α is sorafenib, sunitinib, axitinib, or motesanib.

2. The method of claim 1, wherein said biomarker is PDGFR-α.

3. The method of claim 1, wherein said analyte binding assay is an immunoassay.

4. The method of claim 3, wherein said immunoassay is immunohistochemistry.

5. The method of claim 4, wherein said immunohistochemistry is performed with an automated system or a manual system.

6. The method of claim 1, wherein said biomarker is the PDGFR-α transcript.

7. The method of claim 1, wherein said analyte binding assay is an RNA detecting assay.

8. The method of claim 7, wherein said RNA detecting assay comprises RT-PCR or in situ hybridization.

9. The method of claim 1, wherein said assay results are quantitative or semi-quantitative.

10. The method of claim 1, wherein said processing comprises formalin fixing said sample, paraffin-embedding said sample, snap freezing said sample, treating said sample to isolate DNA, RNA, or protein, or any combination thereof.

11. The method of claim 1, wherein said radio therapy comprises radio iodine ablative therapy.

* * * * *